United States Patent
Griffin et al.

(10) Patent No.: US 10,695,343 B2
(45) Date of Patent: Jun. 30, 2020

(54) METHOD FOR INDUCING A SUSTAINED IMMUNE RESPONSE

(71) Applicant: Immune Therapeutics Inc., Orlando, FL (US)

(72) Inventors: Noreen Griffin, Orlando, FL (US); Fengping Shan, Shenyang (CN); Nicholas Plotnikoff, Ocean City, NJ (US)

( * ) Notice: Subject to any disclaimer, the term of this patent is extended or adjusted under 35 U.S.C. 154(b) by 0 days.

(21) Appl. No.: 16/154,333

(22) Filed: Oct. 8, 2018

(65) Prior Publication Data

US 2019/0321357 A1 Oct. 24, 2019

Related U.S. Application Data

(63) Continuation of application No. 15/437,365, filed on Feb. 20, 2017, now Pat. No. 10,111,870.

(60) Provisional application No. 62/296,759, filed on Feb. 18, 2016.

(51) Int. Cl.
| | |
|---|---|
| *A61K 31/485* | (2006.01) |
| *A61K 45/06* | (2006.01) |
| *A61K 9/00* | (2006.01) |
| *A61K 9/48* | (2006.01) |
| *A61K 9/70* | (2006.01) |
| *A61K 31/513* | (2006.01) |
| *A61K 31/655* | (2006.01) |
| *A61K 31/337* | (2006.01) |
| *A61K 31/52* | (2006.01) |
| *A61K 31/505* | (2006.01) |

(52) U.S. Cl.
CPC .......... *A61K 31/485* (2013.01); *A61K 9/0053* (2013.01); *A61K 9/48* (2013.01); *A61K 9/7007* (2013.01); *A61K 31/337* (2013.01); *A61K 31/513* (2013.01); *A61K 31/655* (2013.01); *A61K 45/06* (2013.01); *A61K 31/505* (2013.01); *A61K 31/52* (2013.01); *Y02A 50/385* (2018.01); *Y02A 50/387* (2018.01); *Y02A 50/389* (2018.01); *Y02A 50/393* (2018.01); *Y02A 50/397* (2018.01); *Y02A 50/409* (2018.01); *Y02A 50/463* (2018.01); *Y02A 50/465* (2018.01); *Y02A 50/475* (2018.01)

(58) Field of Classification Search
CPC .................................................... A61K 31/485
USPC ......................................................... 514/282
See application file for complete search history.

(56) References Cited

U.S. PATENT DOCUMENTS

| | | | | |
|---|---|---|---|---|
| 4,857,533 | A * | 8/1989 | Sherman | A61K 31/485 514/282 |
| 10,111,870 | B2 * | 10/2018 | Griffin | A61K 45/06 |

OTHER PUBLICATIONS

Ni et al., "Clinical application and its immunoregulation mechanism of naltrexone", Guoji Mianyixue Zazhi, vol. 34, No. 4, pp. 284-286 (2011). English Abstract included.*
Ji, "Research on application of low-dose naltrexone for treating chronic pain", Tianjin Huagon, vol. 28, No. 6, pp. 1-3 (2014). English Abstract Included.*
Sandeep et al., "Immediate Drug Release Dosage Form: A Review", Journal of Drug Delivery & Therapeutics, vol. 3, No. 2, pp. 1550161 (2013).*

* cited by examiner

*Primary Examiner* — Kevin E Weddington

(57) ABSTRACT

A method for inducing a sustained immune response in humans or animal patient suffering from human immuno-deficiency virus (HIV) acquired immune deficiency syn-drome (AIDS, autoimmune disease, cancer, inflammation, and neurodegenerative diseases comprises daily administra-tion to such patients a single oral tablet, rapidly dissolving film, capsule, liquid or cream dose of an Immediate release naltrexone composition comprising between about 0.01 to about 10 mg of naltrexone. In order to provide a benefit the naltrexone must be an Immediate release composition com-prising between about 0.01 and about 10 mg of naltrexone.

12 Claims, No Drawings

METHOD FOR INDUCING A SUSTAINED IMMUNE RESPONSE

CROSS-REFERENCE TO RELATED APPLICATIONS

This application is a continuation of U.S. patent application Ser. No. 15/437,365, filed Feb. 20, 2017 which claims priority under 35 U.S.C. § 119(e) to Provisional U.S. Patent Application Ser. No. 62/296,759, filed Feb. 18, 2016. The disclosure of the aforementioned applications is incorporated by reference in its entirety.

FIELD OF THE INVENTION

The present invention relates to methods of inducing a sustained immune response in patients suffering from human immunodeficiency virus (HIV) acquired immune deficiency syndrome (AIDS), autoimmune disease, cancer, inflammation, and neurodegenerative diseases comprising administering a rapidly dissolving film, single oral tablet, capsule, liquid or cream dose of an Immediate release naltrexone composition comprising between about 0.01 to about 10 mg of naltrexone.

BACKGROUND

Immediate release naltrexone composition comprising between about 0.01 and about 10 mg of naltrexone was specifically designed to enhance immunomodulation and anticancer properties with fewer side effects then existing therapies. Clinical Studies have shown that to have an immunomodulating effect naltreoxone must be in an Immediate release formulation and not as timed release or slow release. The Immediate release naltrexone composition comprising between about 0.01 and about 10 mg of naltrexone not only inhibit angiogenesis, but also induce apoptosis and growth arrest in resistant cancer cells. They also prevent the adhesion of cancer cells to bone marrow stromal cells and thereby inhibit the enhanced secretion of migratory factors, such as interleukin (IL)-6, TNF-$\alpha$, and vascular endothelial growth factor.

Where high dose naltrexone and slow release naltrexone between 0.01 mg and 10 mg and an Immediate release naltrexone composition comprises between about 0.01 mg and about 10 mg of naltrexone share commonality in categories of genes and are considered the same drug, the difference in dosing and delivery method of the Immediate release naltrexone of the invention produces a difference in the overall response of the immune system.

For a wide range of drugs, oral dosage forms such as tablets are clearly the preferred form of delivery. This is due to a high level of patient acceptability and compliance (because they provide an accurate dosage and are easy to administer) as well as advantageous characteristics during and after manufacture, such as they typically show satisfactory physical and chemical stability, are convenient for packing, shipping and administering and offer advantages in manufacturing speed and cost.

However, oral dosage forms need carefully designed disintegration characteristics to achieve the desired bioavailability for the incorporated drug, i.e. dissolution must precede absorption, in case of immediate release tablets should disintegrate rapidly after ingestion in order to facilitate dissolution of the drug. Moreover, the drug loading of conventional tablet formulations is often limited due to potential gastrointestinal irritation (caused by locally high concentration) and/or patient compliance (which limits size and shape to achieve easy swallowing). The Naltrexone formulation described which comprises between 0.05 mg and 10 mg requires immediate onset of action. To meet this requirement immediate release dosage forms have been formulated to disintegrate rapidly after administration with enhanced rate of dissolution.

To accomplish this goal tablets were developed using superdisintegrants such as cross linked polyvinylpyrrolidone or crospovidone (Polyplasdone), modified starches such as sodium starch glycolate (e.g. Primogel, Explotab), soy polysaccharides, cross linked alginic acid, gellan gum, xanthan gum, calcium silicates, ion exchange resins such as INDION 414 and modified celluloses such as carboxymethylcellulose (Croscarmellose sodium). These superdisintegrants provide instantaneous disintegration of tablet after administration in stomach. In the case of immediate release liquid dosage forms and parenteral dosage forms the naltrexone formulation described can be a suspension with typical dispersion agents such as hydroxypropyl methylcellulose and AOT (dioctylsulfosuccinate).

Immediate release tablets are those which disintegrate rapidly and dissolve to release the medicaments. Immediate release may be provided for by way of an appropriate pharmaceutically acceptable diluent or carrier, which diluent or carrier does not prolong, to an appreciable extent, the rate of drug release and/or absorption. An Immediate release formulation excludes formulations which are adapted to provide for "modified", "controlled", "sustained", "prolonged", "extended" or "delayed" release of drug. The immediate-release tablets and capsules release the active ingredient within a small period of time, typically less than 30 minutes.

There is a difference in the cell patterns of genes that are altered by the treatment of Immediate release naltrexone of the invention versus high dose naltrexone and slow release low dose naltrexone between 0.01 mg and 10 mg. The differences are important because an Immediate release naltrexone composition which comprises between about 0.01 and about 10 mg of naltrexone acts as an immunomodulator. Since the Immediate release naltrexone described blocks the opiate receptors only for a few hours before it is naturally excreted, what results is a rebound effect; in which both the production and utilization of met (5) enkelphine opiate growth factor are increased. Once the Immediate release naltrexone has been metabolized, the elevated endorphins produced as a result of the rebound effect can now interact with the more-sensitive and more-plentiful receptors and assist in regulating cell growth and immunity. This rebound effect is not observed with either high dose naltrexone or slow release naltrexone. It is the rebound immunomodulatory effect that effects the treatment of treating patients suffering from human immunodeficiency virus (HIV) acquired immune deficiency syndrome (AIDS), Autoimmune Disease, Opportunistic Infections, Cancer, Inflammation, and Neurodegenerative Diseases ("Younger J, Clin. Rheumatol. 2014; 33(4): 451-459. PMCID).

The immune system protects the body against infectious agents, including bacteria, viruses, fungi, and parasites. In addition, the immune system protects against cancer, as well as disease states that result from immune imbalances and opportunistic infections. Stimulation of the immune system by pharmaceuticals is an important approach to the prevention and treatment of diseases associated with immune suppressed states.

The response by the immune system to an immunogen may be depressed as a consequence of certain diseases or pathological conditions. For example, patients infected with the human immunodeficiency virus (HIV-1) may develop acquired immune deficiency syndrome (AIDS) or AIDS related complex (ARC), and thus have depressed immune responses. In addition to patients with HIV/AIDS patients undergoing cancer therapy, suffering from opportunistic infection or inflammatory diseases have a depressed immune system either due to the diseases or caused by the immunosuppressing drug used in the treatment of cancer, autoimmune disease and HIV/AIDS.

Patients with depressed immune systems are more susceptible to pathological infections or malignancies against which a normal immune system would have otherwise provided sufficient protection. Other such immunocompromised individuals include patients with opportunistic infections, autoimmune diseases, cancer, or undergoing X-rays, radiation treatment, surgery, or chemotherapy treatment.

Current treatments used to prevent the development of immunodeficiency in individuals with viral infections, HIV for example, usually involve administration of compounds that inhibit viral DNA synthesis thereby slowing onset of viral-related immunosuppression.

More recent treatments against HIV include administration of protease inhibitors such as saquinovir, nefinavir, ritonavir and indinavir. Cytokine therapy is also used in the treatment of AIDS patients, with research groups having demonstrated efficacy of interleukin-2 (IL2) in elevating the CD4 T-cell subset in HIV positive patients (Kovacs, et al., N. Engl. J. Med., 1996; 335: 1350-1356). Reports have detailed that IL2 can also increase CD8 T-cell count (Schmitz, et al., Science, 1999; 283: 857-860). Unfortunately, the use of IL2 is normally accompanied by major toxicity (Davey, et al., JAMA, 2000; 284: 183-189). Many of these same drugs are used to treat cancer, autoimmune disease and neurodegenerative diseases.

Nevertheless, given the potential promise of these therapies directed toward anti-retroviral effects, none have proven to be totally effective in treating or preventing development of AIDS. In addition, many of these compounds cause adverse side effects including "black box" warnings of the risk of hematological, toxicity, myopathy, lactic acidosis hepatic decompensating, lactic acidosis, severe hepatomegaly with steatosis and exacerbation of hepatitis B, Drug interaction leading to serious and life threating reactions, including sedative hypnotics, etc; hepatic metabolism, skin reactions low platelet count, diarrhea, nausea, renal toxicity, and bone marrow cytopenia. Numerous clinical studies with low dose naltrexone in normal volunteers, HIV positive, multiple sclerosis, autism, fibromyalgia, diabetes, and cancer patients showed no major toxicity.

Current treatments used to prevent the development of immunodeficiency in individuals with autoimmune disease, Crohn's Disease, multiple sclerosis and cancer, for example, usually involve administration of compounds that slow or suppress the immune system response in an attempt to stop the inflammation involved in the autoimmune attack are called immunosuppressive medications. These drugs include corticosteroids (prednisone), methotrexate, cyclophosphamide, azathioprine, and cyclosporin. Unfortunately, these medications also suppress the ability of the immune system to fight infection and have other potentially serious side effects.

More recent treatments against autoimmune diseases and cancer include administration of glucocorticoids, cytostatics are nitrogen mustards (cyclophosphamide), nitrosoureas, platinum compounds, interferons and TNF binding proteins.

Nevertheless, given the potential promise of these therapies directed toward autoimmune disease and cancer, none have proven to be totally effective in treating or preventing development of autoimmune disease or cancer. In addition, many of these compounds cause adverse side effects including "black box" warnings of the risk of hematological, toxicity, myopathy, lactic acidosis hepatic decompensating, lactic acidosis, severe hepatomegaly with steatosis and exacerbation of hepatitis B, Drug interaction leading to serious and life threating reactions, including sedative hypnotics, etc; hepatic metabolism, skin reactions low platelet count, diarrhea, nausea, renal toxicity, and bone marrow cytopenia. Numerous clinical studies with Immediate release naltrexone dosed between 0.01 mg and 10 mg in normal volunteers, HIV positive, multiple sclerosis, autism, fibromyalgia, diabetes, and cancer patients showed no major toxicity.

Thus, there exists a need in the art for improved methods of stimulating a sustained immune system response in patients in need of such treatment, such as patients include those with compromised immune system responses (e.g. the potential to develop compromised immune system responses HIV-infected (e.g. AIDS patients), opportunistic infections, autoimmune disease, cancer, cardio vascular disease, inflammatory diseases, and neurodegenerative diseases.

It is therefore unexpected that an Immediate release naltrexone composition comprising between about 0.01 mg and about 10 mg of naltrexone could be used in methods of treatment useful in producing a sustained immune response in a patient comprising administering the active agents on dosage schedule to a patient in need of such treatment.

It is also surprising that an Immediate release naltrexone composition comprising between about 0.01 mg and about 10 mg of naltrexone is effective in promoting a sustained cell increase in immune system response including sustained cell levels.

The present invention provides for, inter alia, methods of treatment useful for inducing a sustained immune system response in an immunocompromised patient in need of such treatment wherein the method comprises administering to the patient an Immediate release naltrexone composition comprising between about 0.01 mg and about 10 mg of naltrexone, either alone, combined, or in further combination with other compounds useful for increasing immune system response, including vaccines. In this context, "immunocompromised" refers to any reduction in T-cell number or function.

The present invention also provides for, inter alia, methods of treatment useful for inducing a sustained immune system response in an HIV-infected patient, wherein the method comprises administering to the HIV-infected patient an Immediate release naltrexone composition comprising between about 0.01 mg and about 10 mg of naltrexone, either alone, combined, or in further combination with other compounds useful for slowing the progression of HIV proliferation or HIV-associated infections, such as abacavir, didanosine, emtricitabine, lamivudine, stavudine, tenofovir disoproxil fumarate, zidovudine (AZT), atazanavir, darunavir, fosamprenavir, indinavir, nelfinavir, ritonavir, saquinavir, tipranavir, enfuviritide, maraviroc, dolutegravir, elvitegravir, raltegravir, cobicistat, efavirenz, nevirapine, etravirine and rilpivine. Combination HIV therapies are also included to be administered with the naltrexone formulation described such as abacavir and lamivudine; abacavir, dolutegravir and lamivudine; abacavir lamivudine and zidovudine; atazanavir and cobicistat; darunavir and cobicistat; efavirenz, emtricitabine and tenofovir disoproxil fumarate;

elvitegravir, cobicistat, emtricitabine, tenofovir alafenamide fumerate; elvitegravir, cobicistat, emtricitabine and tenofovir disoproxil fumerate; emtricitabine, rilpivirine and tenofovir alafenamide; emtricitabine, rilpivirine and tenofovir disoproxil fumerate; emtricitabine and tenofovir alafenamide; emtricitabine and tenofovir disoproxil fumerate; lamivudine and zidovudine; and lopinavir and ritonavir. Additionally, cytokines such as G-CSF, IL-11, IL-12, IL-2; and gamma interferon and antibiotics or other drugs used for the treatment or prevention of infections in HIV-infected patients. Administration to such patients comprises a single oral, liquid or cream dose of an Immediate release naltrexone composition comprising between about 0.01 mg to about 10 mg of naltrexone. It is known that for naltrexone blocks the opiate receptor, but the effect on the immune system only occurs when the opiate receptor is blocked for a short period of time which requires the naltrexone be an Immediate release naltrexone composition comprising between about 0.01 mg and about 10 mg of naltrexone to have an immunomodulatory effect.

The Immediate release naltrexone composition comprising between about 0.01 mg and about 10 mg of naltrexone was specifically designed to enhance immunomodulation and anticancer properties but with less side effects. (Mohammad A. Seifrabiei, Mohammad Abbasi, Ali Montazeri, Fatemeh Shahnazari and Arash Pooya *American Journal of Applied Sciences* 5 (7): 872-875, 2008.)

Clinical Studies reveal that an Immediate release naltrexone composition comprising between about 0.01 and about 10 mg of naltrexone not only inhibit angiogenesis but also induce apoptosis and growth arrest in resistant cancer cells. They also prevent the adhesion of cancer cells to bone marrow stromal cells and thereby inhibit the enhanced secretion of migratory factors, such as interleukin (IL)-6, TNF-α, and vascular endothelial growth factor. In research experiments, ovarian cancer cells were treated with either water as the control or different dosing regimens of naltrexone to replicate high dose versus Immediate release dosing of naltrexone. Using the Immediate release low or short-term dosing composition of naltrexone it was observed that the growth of cancer cells was slowed; however, when a high dose of naltrexone was used, cancer cells were stimulated and grew faster.

Autoimmune disease, cancer, cardiovascular disease, inflammatory bowel disease, Musculo-skeletal disorders, metabolic disorders and neuro degenerative diseases develop when the immune system begins to dysfunction which can be caused by a number of factors. When an organism mounts an anti-self response, usually as a result of abnormalities of the afferent parts of the immune system which are involved in antigen-specific responses and chronic inflammation which can be can be triggered by cellular stress and dysfunction, such as that caused by excessive calorie consumption, environmental factors, elevated blood sugar levels, and oxidative stress. It is now clear that the destructive capacity of chronic inflammation is unprecedented among physiologic processes (Karin et al. 2006). Chronic inflammation is caused by a causative agent, non-degradable pathogens that cause persistent inflammation, infection with some types of viruses, persistent foreign bodies, overactive immune system reactions and it causes major cells involvement—macrophages, lymphocytes, plasma cells (these three are mononuclear cells), and fibroblast with primary mediators—reactive oxygen species, hydrolytic enzymes, IFN-γ and other cytokines, growth factor and long term inflammation causes the destruction of tissue, thickening and scarring of connective tissue (fibrosis), death of cells or tissues (necrosis).

Naltrexone when used in Immediate releasing composition comprising between about 0.01 mg to about 10 mg of naltrexone is an immune-modulating drug and as such has more then one mechanism of action in the treatment of immune deficiency diseases, opportunistic infections, autoimmune disease, cancer, cardio vascular disease, chronic infections, inflammatory diseases, inflammatory bowel disease, musculo-skeletal disorders, metabolic disorders and neurodegenerative diseases. As an immune-modulating drug, naltrexone has a cascade benefit effect on the immune system.

As an immunomodulatory drug, Immediate release naltrexone comprising between about 0.01 mg and about 10 mg of naltrexone works by binding for a short period of time with mu receptors. An Immediate release naltrexone composition comprising between about 0.01 mg and about 10 mg has an affinity to at least a million extremely specific delta receptors. An Immediate release naltrexone composition comprising between about 0.01 mg and about 10 mg of naltrexone has only a weak binding to only one hundred such receptors. An Immediate release naltrexone composition comprising between about 0.01 mg and about 10 mg of naltrexone blocks the mu receptor and upregulates delta receptors so the endorphins released at night binds to the delta not the mu receptors, which results in stimulation of the immune system via delta receptors and the blocking of the mu agonists for longer then 4 to 6 hours suppress the immune system.

The blocking of the mu receptor for a short period causes an increase the products of cytokines including met-enkelphine. This interaction regulates normal cell growth. If too much met-enkelphine or opiate growth fact ("OGF") OGF is released, it slows cell growth and if too little OGF or enkephalin is released the cells proliferate in an out of control manner and have the potential to become cancer cells or overactive immune cells. If the naltrexone dose is too high, or an Immediate release dose composition comprising an amount of naltrexone higher than about 10 mg of naltrexone, then naltrexone is still bound to the opioid receptor and the met-enkephalin cannot interact with the receptor. The end result and risk of taking such compositions is that either there will be no effect or the cancer cell growth High dose naltrexone, slow release low dose naltrexone and Immediate release naltrexone compositions comprising between about 0.01 and about 10 mg of naltrexone share commonality in categories of genes and are considered same drug except for the difference between both the type of delivery and the dose. These factors determine if naltrexone acts as a immunomodulator and is a benefit to immune comprised patients.

An Immediate release naltrexone composition comprising between about 0.01 mg and about 10 mg of naltrexone blocks opiate receptors temporarily (typically 2-4 hours), which leads to rebound increase in endogenous opioids and endorphins but especially in the production of cytokines which are critical to immune health. ("*Critical Regulators of Cytokine Signaling and Immune Responses*", International Congress Series Volume 1285, November 2005, Pages 121-129)

An Immediate Release naltrexone composition comprising between about 0.01 mg and about 10 mg: increases endorphins and inhibits cell proliferation in vivo, while high dose naltrexone or slow release naltrexone decreases endorphins, promotes cell growth, Increases endorphin levels, decreased inflammatory cytokines, shift from Th1 (proinflammatory) to Th2 (anti-inflammatory), reduces production of TNF and begins to effect TRL4 and TRL9 within 72 hours and reduce inflammation. (Faith; Robert E.; Faith, Robert E.; Murgo, Anthony J.; Good, Robert A.; Plotnikoff, Nicholas P. *Cytokines: Stress and Immunity*, Second Edition (Page 362).).

Parallel with OGFR function, as OGF exhibits cancer growth features similar to an Immediate release naltrexone composition comprising between about 0.01 mg and about 10 mg. But continuous 48 h exposure to naltrexone has no dramatic effect in a number of tumors, no effect on pancreatic cancer cells: MIA-PaCa2, PANC1, and BxPC3, no effect on glioma cells: T98G and U87MG, no effect on A549 (lung) and HCT116 (CRC) no effect expression of CDK Inhibitors p15, p18, p19, and p27 are not altered by Immediate release naltrexone.

Continuous exposure naltrexone in a dose between 0.01 mg and 10 mg stimulates the growth of tumors. Treatment with an Immediate release naltrexone composition comprising between about 0.01 mg and about 10 mg of naltrexone inhibit tumor growth, this is associated with the short-term blockade of opioid receptors. This blockade causes a compensatory increase in receptors; however, the result of this differs with dose. An Immediate release naltrexone composition comprising between about 0.01 mg and about 10 mg of naltrexone is associated with cell cycle responses via OGF action on $p16^{INK4a}$ and $p21^{WAF1/CIP}p16$.

The continuous exposure to an Immediate release naltrexone composition comprising between about 0.01 mg and about 10 mg of naltrexone has a dramatic effect in the number of tumors such as pancreatic cancer cells, glioma cells, TRL9, TRL4, and T-cell productions and beta-endorphin levels. The effect on beta-endorphin levels is very important because beta-endorphin levels are reduced to ⅛ to ¼ normal levels in autoimmune related and rheumatic disease as Fibromyalgia, MS, Crohn's Disease, endometriosis, cluster headaches, chronic migraines, lupus, arthritis and gout. An Immediate release naltrexone composition comprising between about 0.01 mg and about 10 mg has been shown to increase beta-endorphines levels, which shifts the balance from Th1 to Th2 cells to decrease inflammation.

Like opiate receptors toll like receptors are present throughout the body. They are part of the bodies first line defense mechanism against invading pathogens (such as viruses, parasites, bacteria, protozoae etc.). Basically, these receptors spot "non-human" proteins and start a defense against them. We found that not all the cytokine expressions by the macrophage were decreased while TLR9 was down-regulated, IL-12, TNF-alpha, IFN-gamma and IL-1beta expressions were significantly decreased, but IL-6, IFN-beta and IL-10 expressions were not affected. Interestingly, the level of IFN-alpha was even increased. This alteration of cytokines produced by TLR9-downregulated APCs upon CpG ODN stimulation might indicate that the role of CpG DNA is more complicated in the pathogenesis and prevention of diseases. In addition, LR2 and TLR9 and co-stimulation of TLRs have been shown to induce HIV replication. Together these results underscore the importance of TLRs in bacterial Ag- and CpG DNA-induced HIV-LTR trans-activation and HIV replication. These observations may be important in understanding the role of the innate immune system and the molecular mechanisms involved in the increased HIV replication and HIV disease progression associated with multiple opportunistic infections. Based on the present evidence, it is likely that TRL9-activated immune responses to the CpG motif in GEM91 were responsible for the observed increases in viral load, and that CpG motif in oligonucleotide phosphorothioates is biologically active. (*J Immunol.* 2003 May 15; 170(10):5159-64.) Toll-like receptor 2 (TLR2) and TLR9 signaling results in HIV-long terminal repeat trans-activation and HIV replication in HIV-1 transgenic mouse spleen cells: implications of simultaneous activation of TLRs on HIV replication.) This supports the premise that low dose naltrexone is useful in the treatment of HIV/AIDS. The connection between an Immediate release naltrexone composition comprising between about 0.01 mg and about 10 mg of naltrexone as effective the regulations of TRL9 in the stopping of the progression of HIV/AIDS and opportunistic infections has not been previously described. (Plotnikoff N P, Wybran J: Methionine-enkephalin Shows Promise in Reducing HIV in Blood. Ann N Y Acad Sci. 1987; 496:108-14.)

It is thought that many autoimmune diseases are caused by feedback loops. For example, chronic infection can cause huge inflammatory response (such as Epstein Barr, Crohn's Disease, IBS, fibromyalgia) and the excess inflammatory response damages cells in the body in the effort to kill the infection.

During this process, the TLR-4 receptors are constantly being stimulated to fight off an infection, which does not exist, because the TLR-4 receptors are being stimulated all the time by natural parts of your blood. This, unfortunately, leads to the body ignoring real infections and the body being induced to attack healthy cells which results in the broad spectrum of autoimmune diseases.

An Immediate release naltrexone composition comprising between about 0.01 mg and about 10 mg reduces nitric oxide synthase activity, inhibits glutamate formation and microglial activity, and reduces proinflammatory cytokine and neurotoxic superoxide production. Filamin A modulates the mu opioid receptor. An Immediate release naltrexone composition comprising between about 0.01 mg and about 10 mg effect adenosine receptors involved in pain signaling and intrathecal adenosine suppresses pain.

It is via the non-opioid antagonist path that an Immediate release naltrexone composition comprising between about 0.01 and about 10 mg of naltrexone exerts its anti-inflammatory effects. Microglia are central nervous system immune cells that are activated by a wide range of triggers. Once activated, microglia produce inflammatory and excitatory factors that can cause such as pain sensitivity, fatigue, cognitive disruption, sleep disorders, mood disorders, and general malaise.

When chronically activated, the resulting pro-inflammatory cascade may become neurotoxic, causing several deleterious effects. Given the wide variety of diseases that are caused by increase inflammatory factors produced by activated microglia (e.g., pro-inflammatory cytokines, substance P, nitric oxide, and excitatory amino acids) a range of symptoms and medical outcomes could share the pathophysiological mechanism of central inflammation. Conditions such as fibromyalgia may involve chronic glial cell activation and subsequent production of pro-inflammatory factors.

The hypothesis is indirectly and partially supported by the high degree of symptomatic overlap between fibromyalgia and cytokine-induced illness. An Immediate release naltrexone composition comprising between about 0.01 and about 10 mg of naltrexone blocks the TLR-4 receptor experimentally, and in vivo. (In a test tube and also humans) Blocking these receptors causes the whole cycle to activate or re-balance and the immune system gradually return too normal. (Faith, R E, Murgo, A J, Good R A, Plotnikoff N P, 2012 Cytokines: Stress and Immunity, Second Edition).

Unfortunately, the TLR-4 receptors probably cannot "unlearn" to react to something, so the treatment with low dose naltrexone is long term and will control the symptoms after varying periods of initial treatment, depending on which set of TLR-4 receptors are malfunctioning. Crohn's patients have positive response due to the number of TLR-4 and TRL-9 receptors in the bowel and intestines. Studies have shown when patients stopped taking an Immediate release naltrexone composition comprising between about 0.01 and about 10 mg of naltrexone have seen the return of the chronic disease and symptoms and when patients resume treatment with an Immediate release naltrexone composition comprising between about 0.01 and about 10 mg the symptoms subside once again.

The central nervous system (CNS) is made up of nerves and glial cells. The function of the glia is to provide immune protection and provide defense to the CNS. Under normal conditions the glia remain in an inactivate state. They become activated readily in response to infection or injury. The most important change that happens during inflammation of the brain and spinal cord (CNS) is activation of glial cells, which explains the effectiveness of an Immediate release naltrexone composition comprising between about 0.01 and about 10 mg of naltrexone helps with neurodegenerative diseases.

When glial cells are activated they trigger the release of certain chemicals known as pro-inflammatory and neurotoxic factors. These factors include several cytokines such as tumor necrosis factor alpha (TNF-$\alpha$) and interleukin one beta (IL1-$\beta$), fatty acid metabolites and free radicals such as nitric oxide and superoxide. In painful conditions such as complex regional pain and fibromyalgia and neuropathic pain, damage to the peripheral nerves shifts the glial cells to an activated state within the spinal cord.

The glial cells are made up of microglia and astrocytes. The microglia guard and protect the immune system and the astrocytes help maintain cell fluid balance which is important for the action of chemicals in the cells called neurotransmitters (needed to control nerve function). Glial cells are activated by trauma, surgery, injury, infection, and opioids. When activated, glial release pro-inflammatory and neurotoxic factors (cytokines). Opiate antagonists that block the effects of opioids and have been shown to help prevent activation of glial cells. Low dose naltrexone has been shown to inhibit the activation of glial cells. (Younger, J et al. Arthritis Rheum. 2013; 65 (2): 529-538)

Immediate release naltrexone has been shown to effect telomeres. Telomeres are inside the nucleus of a cell, our genes are arranged along twisted, double-stranded molecules of DNA called chromosomes. At the ends of the chromosomes are stretches of DNA called telomeres, which protect our genetic data, make it possible for cells to divide, and have been implicated in how we age and get cancer.

Telomeres have been compared with the plastic tips on shoelaces, because they keep chromosome ends from fraying and sticking to each other, which would destroy or scramble an organism's genetic information.

Yet, each time a cell divides, the telomeres get shorter. When telomeres get too short, the cell can no longer divide; it becomes inactive or "senescent" or it dies. This shortening process is associated with aging, cancer, and a higher risk of death.

Clinical studies have shown that telomeres are reduced in human liver tissues with age and chronic inflammation. (Telomere Reduction in Human Liver Tissues with Age and Chronic Inflammation experimental cell research 256(2): 578-582 • April 2000). Immediate release naltrexone is a proven immunomodulator that helps to reset and rebalance balance of the immune system between the cellular (Th1) and the humoral (Th2) immune systems. Immune balance is regulated through T-helper cells that produce cytokines. The Th1 lymphocytes help fight pathogens that are within cells such as viruses and among cells such as cancer through activation of interferon-gamma and macrophages. The Th2 lymphocytes target external pathogens like parasites, allergens, toxins through the activation of B-cells and antibody production therefore reducing chronic inflammation. Immediate release low dose naltrexone has been shown to regulate cytokines causing the modulation of TGF-B, leading to a reduction of Th-17, the promoter of autoimmunity. Low dose naltrexone turns off the cells growth that causes autoimmune dysfunction. Findings demonstrate that cancer cell lines that express functional TLR4 and TLR9 with possible effects on cancer progression and outcome of BCG-based ("*Immunotherapy. J Biol Chem.* 2013 Nov. 15; 288(46): 33171-80. doi: 10.1074/jbc.M113.518175. Epub 2013 Oct. 4. Inhibition of Telomerase Recruitment and Cancer Cell Death. Nakashima M, Nandakumar J, Sullivan K D, Espinosa J M, Cech T R").

An Immediate release naltrexone composition comprising between about 0.01 mg and about 10 mg of naltrexone has been shown in inflammatory bowel disease to halt inflammation due to the shift of Th1 to TH2 which then allow the telomeres to lengthen but at the same time Immediate release naltrexone composition will inhibit growth causing the telomeres too shorten and when the cells can no longer divide; they die. This shortening process is associated with aging, cancer, and a higher risk of death.

Research into the lengthening of telomeres to reduce inflammation indicates that telomeres lengthen in all cells including cancer cells. Immediate release naltrexone is an immunomodulator and when administered in an Immediate release composition comprising between about 0.01 mg and about 10 mg of naltrexone it will lengthen telomeres in cells and therefore reduce inflammation in patients as shown in Crohn's and inflammatory bowel disease patients. Low dose naltrexone is a proven to inhibit cells growth in cancer cells, and could assist in the slowing down of cell death and turn back the aging process by lengthening telomeres. (*Telomere Extension Turns Back Aging Clock in Cultured Human Cells*, Jan. 23, 2015 Stanford University Medical Center. Ramunas, E. Yakubov, J. J. Brady, S. Y. Corbel, C. Holbrook, M Brandt, J. Stein, J. G. Santiago, J. P. Cooke, H. M Blau.

The majority of the currently practiced drug treatments for autoimmune disease, cancer, cardio vascular disease, inflammatory diseases, inflammatory bowel disease, musculo-skeletal disorders, metabolic disorders and neuro degenerative diseases have significant drawbacks. The number of patients taking immunosuppressive drugs for the management of autoimmune inflammatory conditions is increasing. The general practitioner needs to be active in preventing, monitoring and managing the adverse effects of these drugs even long after the treatment has ceased. Monitoring is required because immunosuppressive drugs increase the risks of infection, malignancy, cardiovascular disease and bone marrow suppression. Apart from gastrointestinal disturbances, the nonsteroidal anti-inflammatory drugs have been shown to cause renal toxicity and therefore must be avoided particularly in lupus patients with renal involvement.

The antimalarial may cause serious retinopathy, which can occur several years after initiation of therapy. Chronic glucocorticoid therapy is associated with a number of pernicious side effects, including hypertension, excessive immunosuppression and CNS dysfunction. Immunosuppressive and cytotoxic agent a primary cause or secondary contributor in many cause bone marrow depression and lead to serious diseases, usually as a result of the formation of autoantibodies by the immune system of the organisms, which attack its own cells. Such diseases include, for example, systemic lupus erythematosus, rheumatoid arthritis, autoimmune thyroiditis, autoimmune hemolytic anemia, and certain forms of progressive liver disease. Low dose naltrexone has been shown to increase bone marrow.

Rheumatoid arthritis in its fully developed form is a symmetrical, inflammatory disease of the synovial lining of peripheral joints, which leads to destructive changes. Although arthritis is the most frequent and prominent manifestation, this is a generalized disease involving many body systems. Pathologically, rheumatoid arthritis is an inflammatory disease involving the immune system. Immune complexes (antigen/antibody) form within the joint and activate the complement system. White blood cells are then attracted into the synovial fluid. These cells phagocytose the immune complexes and in so doing release lysosomal enzymes and other chemical mediators of inflammation. Continued inflammation causes the synovium to proliferate and spread over the joint surface. The thickened synovial tissue, called pannus, releases enzymes, which erode both cartilage and bone to cause permanent damage.

Rheumatoid arthritis is treated with many of the same pharmaceutical agents used in systemic lupus. Most patients initially receive nonsteroidal anti-inflammatory drugs, sometimes together other analgesics. Where the disease is not adequately controlled with these agents, disease-modifying antirheumatic drugs, such, D-penicillamine, as well as steroids and biologic agents. Continuing therapy with any or all of the aforementioned categories of drugs can produce a variety of well-known adverse effects, and none of these drugs are significantly effective in achieving true remission of the disease in most patients.

It is known that inflammatory cells such as polymorphonuclear leukocytes have opiate receptors. The endogenous opioid, endorphin has been shown in both animal and human studies to stimulate superoxide radical production by human polymorphonuclear leukocytes via an opiate receptor. This superoxide production has been shown to be stopped by equimolar concentrations of the opiate antagonist naloxone. (B. M. Sharp et al., *J. Pharm. Exp. Ther.*, 242(2):579-582, 1987).

As used herein, the term human immunodeficiency virus, cancer, cardio vascular disease, inflammatory diseases, inflammatory bowel disease, Musculo-skeletal disorders, metabolic disorders and neuro degenerative diseases refers the daily administration of a low dose naltrexone composition comprising between about 0.01 and about 10 mg of naltrexone has been shown to any disease state or condition associated with the shortening of telomerase causing cell death chronic inflammation and immune dysfunction.

SUMMARY OF THE INVENTION

It is the object of the present invention to provide a method for inducing sustained immune response in humans or animal patient suffering from human immunodeficiency virus (HIV) acquired immune deficiency syndrome (AIDS, autoimmune disease, cancer, inflammation, and neurodegenerative diseases which avoids the drawbacks and disadvantages of prior art and present standard of care drug treatment methods while achieving dramatic symptomatic relief and reducing inflammation levels, systemic autoantibody levels increase production of increasing proliferation and functional activities of CD4+ T-cells and CD8+ T-cells which will play a role in anti-virus and anti-tumor activities; increasing maturation of dendritic cells which will initiate and intensify T-cell responses; increasing secretion of cytokines such as IL-2, TNF, IL-12 and IFN-= which will amplify the T-cell response and mediate interaction among immune cells, including the non-opiate receptors like TRL-4 and TRL-9 through forming a modulated and balanced immunity between Th1 and Th2; increasing functions of macrophages, resulting in enhanced cellular immunity through secreting a set of cytokines; and increasing activity of NK cells which have the ability to kill cancer cells and virus-infected cells and lengthen telomers thereby slowing cell death. In cancer, an Immediate release naltrexone composition comprising between about 0.01 and about 10 mg of naltrexone enhances maturation of bone marrow dendritic cells "(BMDCs) Meng J, Meng Y, Plotnikoff N P, Youkilis G, Griffin N, Shan F.—*Low dose naltrexone enhances maturation of bone marrow dendritic cells (BMDCs). Int Immunopharmacol.* 2013 December; 17(4):1084") which is important when patients are undergoing any immunosupression therapy as low dose naltrexone can held offset the toxic side effects of these treatments.

The differences between naltrexone at higher than about 11 mg to 300 mg and naltrexone between 0.01 and 10 mg slow release and Immediate release between 1 mg and 10 mg have not been previously recognized. The surprising characteristics of Immediate release naltrexone between 0.01 mg and 10 mg such as its effect on telomeres and increase production of increasing proliferation and functional activities of CD4+ T-cells and CD8+ T-cells which play a role in anti-virus and anti-tumor activities; increasing maturation of dendritic cells which will initiate and intensify T-cell responses; increasing secretion of cytokines such as IL-2, TNF, IL-12 and IFN-γ which will amplify the T-cell response and mediate interaction among immune cells, including TRL-4 and TRL-9 forming a modulated and balanced immunity; increasing functions of macrophages, resulting in enhanced cellular immunity through secreting a set of cytokines; and increasing activity of NK cells which have the ability to kill cancer cells, increase viral load, effect LR2 and TLR9 to slow down the HIV replication and virus-infected cells, lengthen telomers slowing cell death.

The invention provides a method for treating or preventing viral infections comprising administering to a mammal in need thereof an Immediate release pharmaceutical composition comprising between about 0.01 mg and about 10.0 mg of naltrexone or a pharmaceutically acceptable salt thereof alone or in combination with one or more anti-viral agents. The antiviral agent is selected from the group consisting of an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, and an antibody therapy (monoclonal or polyclonal).

The invention further provides that the viral infection is chosen from the group consisting of molluscum contagiosum infection, HTLV infection, HTLV-1 infection, hepatitis-A, HCV, HBV, HIV/AIDS infection, human papilloma virus infection, herpes virus infection, genital herpes infection, viral dysentery, flu, measles, rubella, chickenpox, mumps, polio, rabies, mononucleosis, ebola, respiratory syncytial virus, dengue fever, yellow fever, lassa fever, arena virus, bunyavirus, Filovirus, flavivirus, hantavirus, rotavirus, viral meningitis, west Nile fever, arbovirus, parainfluenza, smallpox, Epstein-Barr virus, dengue hemorrhagic fever, cytomegalovirus, infant cytomegalic virus, progressive multifocal leukoencephalopathy, viral gastroenteritis, a hepatitis, cold sores, ocular herpes, meningitis, encephalitis, shingles, encephalitis, California serogroup viral, St. Louis encephalitis, rift valley fever, hand, foot, & mouth disease, hendra virus, enteroviruses, astrovirus, adenoviruses, Japanese encephalitis, lymphocytic choriomeningitis, roseola infantum, sandfly fever, SARS, warts, cat scratch disease, slap-cheek syndrome, orf, pityriasis rosea and lyssavirus. Preferably the viral infection to be treated or prevented is HIV/AIDS infection. the Preferably the additional anti-viral agent is chosen from the group consisting of abacavir, didanosine, emtricitabine, lamivudine, stavudine, tenofovir disoproxil fumarate, zidovudine (AZT), atazanivir, darunavir, fosamprenavir, indinavir, nelfinavir, ritonavir, saquinavir, tipranavir, enfuviritide, maraviroc, dolutegravir, elvitegravir, raltegravir, cobicistat, efavirenz, nevirapine and etravirine or the combinations rilpivine abacavir and lamivudine; abacavir, dolutegravir and lamivudine; abacavir lamivudine and zidovudine; atazanavir and cobicistat; darunavir and cobicistat; efavirenz, emtricitabine and tenofovir disoproxil fumarate; elvitegravir, cobicistat, emtricitabine, tenofovir alafenamide fumerate; elvitegravir, cobicistat, emtricitabine and tenofovir disoproxil fumerate; emtricitabine, rilpivirine and tenofovir alafenamide; emtricitabine, rilpivirine and tenofovir disoproxil fumerate; emtricitabine and tenofovir alafenamide; emtricitabine and tenofovir disoproxil fumerate; lamivudine and zidovudine; and lopinavir and ritonavir.

The invention further provides a method for treating or preventing viral infections comprising administering to a mammal in need thereof an Immediate release pharmaceutical composition comprising between about 0.01 mg and about 8.0 mg of naltrexone or a pharmaceutically acceptable salt thereof.

The invention further provides a method for treating or preventing viral infections comprising administering to a mammal in need thereof an Immediate release pharmaceutical composition comprising between about 0.01 mg and about 6.0 mg of naltrexone or a pharmaceutically acceptable salt thereof.

The invention further provides a method for treating or preventing viral infections comprising administering to a mammal in need thereof an Immediate release pharmaceutical composition comprising between about 0.01 mg and about 4.5 mg of naltrexone or a pharmaceutically acceptable salt thereof.

The invention also provides for an administration is once in a 24 hour period.

The invention also provides that the mammal is a human.

The invention also provides that the pharmaceutically acceptable salt of naltrexone is the hydrochloride salt.

The invention also provides a method of treating or preventing viral infection using an Immediate release composition which releases the pharmaceutically acceptable salt of naltrexone completely within about 60 minutes.

The invention also provides that the administration route is chosen from the group consisting of oral, sublingual, subcutaneous, intramuscular, intravenous, topical, local, intratracheal, intranasal, transdermal and rectal administration.

The invention also provides a method of treating or preventing viral infection using an Immediate release composition of naltrexone in the form of a rapidly dissolving film, capsules (including soft gel) or tablet.

The invention provides a method for treating or preventing cancer comprising administering to a mammal in need thereof an Immediate release pharmaceutical composition comprising between about 0.01 mg and about 10.0 mg of naltrexone or a pharmaceutically acceptable salt thereof alone or in combination with one or more anti-cancer agents or radiation.

The invention further provides a method for treating cancer comprising administering to a mammal in need thereof an Immediate release pharmaceutical composition comprising between about 0.01 mg and about 8.0 mg of naltrexone or a pharmaceutically acceptable salt thereof.

The invention further provides a method for treating cancer comprising administering to a mammal in need thereof an Immediate release pharmaceutical composition comprising between about 0.01 mg and about 6.0 mg of naltrexone or a pharmaceutically acceptable salt thereof.

The invention further provides a method for treating cancer comprising administering to a mammal in need thereof an Immediate release pharmaceutical composition comprising between about 0.01 mg and about 4.5 mg of naltrexone or a pharmaceutically acceptable salt thereof.

The invention further provides a method of treating or preventing cancer where the cancer is chosen from the group consisting of malignant tumors, benign tumors, solid tumors, sarcomas, carcinomas, hyperproliferative disorders, carcinoids, Ewing sarcomas, Kaposi sarcomas, brain tumors, tumors originating from the brain and/or the nervous system and/or the meninges, gliomas, glioblastomas, neuroblastomas, stomach cancer, kidney cancer, kidney cell carcinomas, prostate cancer, prostate carcinomas, connective tissue tumors, soft tissue sarcomas, pancreas tumors, liver tumors, head tumors, neck tumors, laryngeal cancer, esophageal cancer, thyroid cancer, osteosarcomas, retinoblastomas, thymoma, testicular cancer, lung cancer, lung adenocarcinoma, small cell lung carcinoma, bronchial carcinomas, breast cancer, intestinal cancer, colorectal tumors, colon carcinomas, rectum carcinomas, gynaecological tumors, ovary tumors/ovarian tumors, uterine cancer, cervical cancer, cervix carcinomas, cancer of body of uterus, corpus carcinomas, endometrial carcinomas, urinary bladder cancer, urogenital tract cancer, bladder cancer, skin cancer, epithelial tumors, squamous epithelial carcinoma, basaliomas, spinaliomas, melanomas, intraocular melanomas, leukemias, monocyte leukemia, chronic leukemias, chronic myelotic leukemia, chronic lymphatic leukemia, acute leukemias, acute myelotic leukemia, acute lymphatic leukemia and lymphomas.

The invention also provides for an administration is once in a 24 hour period.

The invention also provides that the mammal is a human.

The invention also provides that the pharmaceutically acceptable salt of naltrexone is the hydrochloride salt.

The invention also provides a method of treating cancer using an Immediate release composition which releases the pharmaceutically acceptable salt of naltrexone completely within about 60 minutes.

The invention also provides that the administration route is chosen from the group consisting of oral, sublingual, subcutaneous, intramuscular, intravenous, topical, local, intratracheal, intranasal, transdermal and rectal administration.

The invention also provides a method of treating cancer using an Immediate release composition of naltrexone in the form of a rapidly dissolving films, capsules (including soft gel) or tablet.

The invention further provides that the anti-cancer agents are chosen from the group consisting of genotoxic agents, mitotic poisons, anti-metabolites, proteasome inhibitors, kinase inhibitors and antibodies.

The invention further provides that the anti-cancer agents are chosen from the group consisting of abarelix, aldesleukin, alemtuzumab, alitretinoin, allopurinol, altretamine, amifostine, anastrozole, arsenic trioxide, asparaginase, azacitidine, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cisplatin, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, erlotinib, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, and zoledronic acid.

The invention also provides a method for treating autoimmune and inflammatory diseases comprising administering to a mammal in need thereof an Immediate release pharmaceutical composition comprising between about 0.01 mg and about 10.0 mg of naltrexone or a pharmaceutically acceptable salt thereof.

The invention also provides a method for treating autoimmune and inflammatory diseases comprising administering to a mammal in need thereof an Immediate release pharmaceutical composition comprising between about 0.01 mg and about 8.0 mg of naltrexone or a pharmaceutically acceptable salt thereof.

The invention further provides a method for treating or preventing autoimmune and inflammatory diseases comprising administering to a mammal in need thereof an Immediate release pharmaceutical composition comprising between about 0.01 mg and about 6.0 mg of naltrexone or a pharmaceutically acceptable salt thereof.

The invention also provides a method for treating autoimmune and inflammatory diseases comprising administering to a mammal in need thereof between about 0.01 mg and about 4.5 mg of naltrexone or a pharmaceutically acceptable salt thereof in an Immediate release formulation.

The invention also provides that the autoimmune and inflammatory diseases are chosen from the group consisting of allergic diseases, amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmopathy and asthma, bone marrow or organ transplant rejection or graft-versus-host disease, transplantation of organs or tissue, graft-versus-host diseases brought about by transplantation, Hashimoto's thyroiditis, multiple sclerosis, systemic sclerosis, myasthenia gravis, uveitis, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, acne, alopecia areata, keratoconjunctivitis, vernal conjunctivitis, uveitis associated with Behcet's disease, keratitis, herpetic keratitis, conical cornea, dystrophia epithelialis comeae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, chronic obstructive pulmonary disorder (COPD), bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, trauma, Blephartis, and chronic bacterial infection.

The invention also provides for administration once in a 24 hour period.

The invention also provides a method where the mammal is a human.

The invention also provides that the method uses the hydrochloride salt of naltrexone.

The invention also provides a method using an Immediate release composition that releases the pharmaceutically acceptable salt of naltrexone completely within about 60 minutes.

The invention also provides a method where the administration is chosen from the group consisting of oral, sublingual, subcutaneous, intramuscular, intravenous, topical, local, intratracheal, intranasal, transdermal and rectal administration.

The invention also provides for a method where the Immediate release formulation is in the form of a rapidly dissolving film, capsule (including soft gel) or tablet.

The invention also provides a method for treating disorders of the central nervous system comprising administering to a mammal in need thereof an Immediate release pharmaceutical composition comprising between about 0.01 mg and about 10.0 mg of naltrexone or a pharmaceutically acceptable salt thereof.

The invention also provides a method for treating disorders of the central nervous system comprising administering to a mammal in need thereof an Immediate release pharmaceutical composition comprising between about 0.01 mg and about 8.0 mg of naltrexone or a pharmaceutically acceptable salt thereof.

The invention also provides a method for treating disorders of the central nervous system comprising administering to a mammal in need thereof an Immediate release pharmaceutical composition comprising between about 0.01 mg and about 6.0 mg of naltrexone or a pharmaceutically acceptable salt thereof.

The invention also provides a method for treating or preventing disorders of the central nervous system comprising administering to a mammal in need thereof an Immediate release pharmaceutical composition comprising between about 0.01 mg and about 4.5 mg of naltrexone or a pharmaceutically acceptable salt thereof.

The invention also provides a method for treating a disorder of the central nervous system chosen from the group consisting of schizophrenia, schizoaffective disorders, schizophreniform disorders, delusional syndromes and other psychotic conditions related and not related to taking psychoactive substances, affective disorder, bipolar disorder, mania, depression, anxiety disorders of various aetiology, stress reactions, conciousness disorders, coma, delirium of alcoholic or other aetiology, aggression, psychomotor agitation and other conduct disorders, sleep disorders of various aetiology, withdrawal syndomes of various aetiology, addiction, pain syndromes of various aetiology, intoxication with psychoactive substances, cerebral circulatory disorders of various aetiology, psychosomatic disorders of various artiology, conversion disorders, dissociative disorders, urination disorders, autism and other developmental disorders, including nocturia, stuttering, tics, cognitive disorders of various types, including Alzheimer's disease, Parkinson disease, psychopatological symptoms and neurological disorders in the course of other diseases of the central and peripheral nervous systems.

The invention also provides for a method where the administration is once in a 24 hour period.

The invention also provides for a method of treating a human.

The invention also provides for a method where the pharmaceutically acceptable salt is the hydrochloride salt of naltrexone.

The invention also provides a method where the Immediate release formulation releases the pharmaceutically acceptable salt of naltrexone completely within about 60 minutes.

The invention also provides a method where the administration is chosen from the group consisting of oral, sublingual, subcutaneous, intramuscular, intravenous, topical, local, intratracheal, intranasal, transdermal and rectal administration.

The invention also provides a method where the Immediate release formulation is in the form of a rapidly dissolving film, capsules (including soft gel) or tablet.

The invention also provides a method for treating cardiovascular disorders comprising administering to a mammal in need thereof an Immediate release pharmaceutical composition comprising between about 0.01 mg and about 10.0 mg of naltrexone or a pharmaceutically acceptable salt thereof.

The invention also provides a method for treating or preventing cardiovascular disorders comprising administering to a mammal in need thereof between about 1.0 mg and about 8.0 mg of naltrexone or a pharmaceutically acceptable salt thereof in an Immediate release formulation.

The invention also provides a method for treating cardiovascular disorders comprising administering to a mammal in need thereof between about 0.05 mg and about 6.0 mg of naltrexone or a pharmaceutically acceptable salt thereof in an Immediate release formulation.

The invention also provides a method for treating cardiovascular disorders comprising administering to a mammal in need thereof between about 0.05 mg and about 4.5 mg of naltrexone or a pharmaceutically acceptable salt thereof in an Immediate release formulation.

The invention also provides a method where the cardiovascular disorder is chosen from the group consisting of myocardial infarction, stroke, thrombosis, hypertension, heart failure, cardiomyopathy, myocarditis, vascular stenosis, restenosis, atherosclerosis and arterial hyperplasia.

The invention also provides a method where the administration is once in a 24 hour period.

The invention also provides a method of treatment of a human.

The invention also provides a method where the pharmaceutically acceptable salt is the hydrochloride salt of naltrexone.

The invention also provides a method using an Immediate release composition that releases the pharmaceutically acceptable salt of naltrexone completely within about 60 minutes.

The invention also provides a method where the route of administration is chosen from the group consisting of oral, sublingual, subcutaneous, intramuscular, intravenous, topical, local, intratracheal, intranasal, transdermal and rectal administration.

The invention also provides a method where the Immediate release composition is in the form of a rapidly dissolving film, capsules (including soft gel) or tablet.

The invention also provides a method for modulating the length of telomeres in the cells of a mammal comprising administering an Immediate release pharmaceutical composition comprising between about 0.01 mg and about 10.0 mg of naltrexone or a pharmaceutically acceptable salt thereof.

The invention also provides a method where the modulation of telomeres is an increase or stabilization of telomere length.

The invention also provides a method for modulating the length of telomeres in the cells of a mammal comprising administering an Immediate release pharmaceutical composition comprising between about 0.01 mg and about 8.0 mg of naltrexone or a pharmaceutically acceptable salt thereof.

The invention also provides a method for modulating the length of telomeres in the cells of a mammal comprising administering an Immediate release pharmaceutical composition comprising between about 0.01 mg and about 6.0 mg of naltrexone or a pharmaceutically acceptable salt thereof.

The invention also provides a method for modulating the length of telomeres in the cells of a mammal comprising administering an Immediate release pharmaceutical composition comprising between about 0.01 mg and about 4.5 mg of naltrexone or a pharmaceutically acceptable salt thereof.

The invention also provides a method where the administration is once in a 24 hour period.

The invention also provides a method where the mammal is a human.

The invention also provides a method where the pharmaceutically acceptable salt is the hydrochloride salt of naltrexone.

The invention also provides a method where the Immediate release composition releases the pharmaceutically acceptable salt of naltrexone completely within about 60 minutes.

The invention also provides a method where the administration is chosen from the group consisting of oral, sublingual, subcutaneous, intramuscular, intravenous, topical, local, intratracheal, intranasal, transdermal and rectal administration.

The invention also provides a method where the Immediate release composition is in the form of a rapidly dissolving film, capsule (including soft gels) or tablet.

The invention also provides a method for inhibiting angiogenesis in a mammal comprising administering an Immediate release pharmaceutical composition comprising between about 0.01 mg and about 10.0 mg of naltrexone or a pharmaceutically acceptable salt thereof.

The invention also provides a method for inhibiting angiogenesis in a mammal comprising administering an Immediate release pharmaceutical composition comprising between about 0.01 mg and about 8.0 mg of naltrexone or a pharmaceutically acceptable salt thereof.

The invention also provides a method for inhibiting angiogenesis in a mammal comprising administering an Immediate release pharmaceutical composition comprising between about 0.01 mg and about 6.0 mg of naltrexone or a pharmaceutically acceptable salt thereof.

The invention also provides a method for inhibiting angiogenesis in a mammal comprising administering an Immediate release pharmaceutical composition comprising between about 0.01 mg and about 4.5 mg of naltrexone or a pharmaceutically acceptable salt thereof.

The invention also provides a method where the administration is once in a 24 hour period.

The invention also provides a method of treatment of a human.

The invention also provides a method where the pharmaceutically acceptable salt is the hydrochloride salt of naltrexone.

The invention also provides a method where the Immediate release composition releases the pharmaceutically acceptable salt of naltrexone completely within about 60 minutes.

The invention also provides a method where the administration is chosen from the group consisting of oral, sublingual, subcutaneous, intramuscular, intravenous, topical, local, intratracheal, intranasal, transdermal and rectal administration.

The invention also provides a method where the Immediate release composition is in the form of a rapidly dissolving film, capsule (including soft gel) or tablet.

The invention also provides a method for inducing a sustained immune response in a mammal comprising administering an Immediate release pharmaceutical composition comprising between about 0.01 mg and about 10.0 mg of naltrexone or a pharmaceutically acceptable salt thereof.

The invention also provides a method for inducing a sustained immune response in a mammal comprising administering an Immediate release pharmaceutical composition comprising between about 0.01 mg and about 8.0 mg of naltrexone or a pharmaceutically acceptable salt thereof.

The invention also provides a method for inducing a sustained immune response in a mammal comprising administering an Immediate release pharmaceutical composition comprising between about 0.01 mg and about 6.0 mg of naltrexone or a pharmaceutically acceptable salt thereof.

The invention also provides a method for inducing a sustained immune response in a mammal comprising administering an Immediate release pharmaceutical composition comprising between about 0.01 mg and about 4.5 mg of naltrexone or a pharmaceutically acceptable salt thereof.

The invention also provides a method where the administration is once in a 24 hour period.

The invention also provides a method where the mammal is a human.

The invention also provides a method where the pharmaceutically acceptable salt is the hydrochloride salt of naltrexone.

The invention also provides a method where the Immediate release composition releases the pharmaceutically acceptable salt of naltrexone completely within about 60 minutes.

The invention also provides a method where the administration is chosen from the group consisting of oral, sublingual, subcutaneous, intramuscular, intravenous, topical, local, intratracheal, intranasal, transdermal and rectal administration.

The invention also provides a method where the Immediate release composition is in the form of a rapidly dissolving film, capsule (including soft gels) or tablet.

Terms and Definitions Used

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refers to derivatives of the disclosed compounds wherein the parent compound is modified by making acid or base salts thereof.

Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals such as aluminium, calcium, lithium, magnesium, potassium, sodium, zinc and the like (see Pharmaceutical salts, Berge, S. M. et al., *J. Pharm. Sci.*, (1977), Vol. 66, pp. 1-19). Pharmaceutically acceptable salts of the present invention can be synthesized from the parent compound, which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the naltrexone (e.g. trifluoro acetate salts), also comprise a part of the invention.

Typically, a pharmaceutically acceptable salt of a compound of naltrexone may be readily prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of naltrexone and the resulting mixture evaporated to dryness (lyophilized) to obtain the acid addition salt as a solid. Alternatively, a compound of naltrexone may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

The acid addition salts of the compounds of naltrexone may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the invention.

Also included are both total and partial salts, that is to say salts with 1, 2 or 3, preferably 2, equivalents of base per mole of acid of formula I or salts with 1, 2 or 3 equivalents, preferably 1 equivalent, of acid per mole of base of formula I.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The salts of naltrexone may form solvates (e.g., hydrates) and the invention also includes all such solvates. The meaning of the word "solvates" is well known to those skilled in the art as a compound formed by interaction of a solvent and a solute (i.e., solvation). Techniques for the preparation of solvates are well established in the art (see, for example, Brittain. *Polymorphism in Pharmaceutical Solids*. Marcel Decker, New York, 1999.).

The invention also encompasses prodrugs of the compounds of formula I, i.e., compounds which release an active parent drug (naltrexone) in vivo when administered to a mammalian subject. A prodrug is a pharmacologically active or more typically an inactive compound that is converted into a pharmacologically active agent by a metabolic transformation. Prodrugs of naltrexone are prepared by modifying functional groups present in naltrexone in such a way that the modifications may be cleaved in vivo to release the parent compound. In vivo, a prodrug readily undergoes chemical changes under physiological conditions (e.g., are acted on by naturally occurring enzyme(s)) resulting in liberation of the pharmacologically active agent. Prodrugs of naltrexone wherein a hydroxyl or amino, of naltrexone is bonded to any group that may be cleaved in vivo to regenerate the free hydroxyl, amino or carboxy group, respectively. Examples of prodrugs include esters (e.g., acetate, formate, and benzoate derivatives) of compounds of formula I or any other derivative, which upon being brought to the physiological pH or through enzyme action is converted to the active parent drug. Conventional procedures for the selection and preparation of suitable prodrug derivatives are described in the art (see, for example, Bundgaard. *Design of Prodrugs*. Elsevier, 1985). Prodrugs may be administered in the same manner as the active ingredient to which they convert or they may be delivered in a reservoir form, e.g., a transdermal patch or other reservoir which is adapted to permit (by provision of an enzyme or other appropriate reagent) conversion of a prodrug to the active ingredient slowly over time, and delivery of the active ingredient to the patient.

The term "carrier" refers to a diluent, excipient, and/or vehicle with which an active compound is administered. The pharmaceutical compositions of the invention may contain combinations of more than one carrier. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

Naltrexone may be formulated for administration in any convenient way for use in human or veterinary medicine and the invention therefore includes within its scope pharmaceutical compositions comprising a compound of the invention adapted for use in human or veterinary medicine. Such compositions may be presented for use in a conventional manner with the aid of one or more suitable carriers. Acceptable carriers for therapeutic use are well-known in the pharmaceutical art, and are described, for example, in Remington's Pharmaceutical Sciences, Mack Publishing Co. (A. R. Gennaro edit. 1985). The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

Pharmaceutical Compositions Comprising Naltrexone

While it is possible that a naltrexone may be administered as the bulk substance, it is preferable to present the active ingredient in a pharmaceutical formulation, e.g., wherein the agent is in admixture with a pharmaceutically acceptable carrier selected with regard to the intended route of administration and standard pharmaceutical practice.

Accordingly, the invention further provides a pharmaceutical composition comprising naltrexone or pharmaceutically acceptable salt thereof in admixture with a pharmaceutically acceptable carrier. The term "carrier" refers to a diluent, excipient, and/or vehicle with which an active compound is administered.

Naltrexone may be used in combination with other therapies and/or active agents.

Accordingly, the invention provides, in a further aspect, a pharmaceutical composition comprising naltrexone or a solvate, hydrate, enantiomer, diastereomer, N-oxide or pharmaceutically acceptable salt thereof, a second active agent, and a pharmaceutically acceptable carrier.

The pharmaceutical compositions may comprise as, in addition to, the carrier any suitable binder, lubricant, suspending agent, coating agent and/or solubilizing agent. Preservatives, stabilizers, dyes and flavoring agents also may be provided in the pharmaceutical composition. Antioxidants and suspending agents may be also used.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see WO02/00196.

The term "Immediate release" is defined as a release of compound from a dosage form in a relatively brief period of time, generally up to about 60 minutes.

Routes of Administration and Unit Dosage Forms

The routes for administration include oral (e.g., as a tablet, capsule, or as an ingestible solution), topical, mucosal (e.g., as a nasal spray or aerosol for inhalation), nasal, parenteral (e.g., by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, epidural and sublingual. The compositions of the invention may be especially formulated for any of those administration routes. In preferred embodiments, the pharmaceutical compositions of the invention are formulated in a form that is suitable for oral delivery.

There may be different composition/formulation requirements depending on the different delivery systems. It is to be understood that not all of the compounds need to be administered by the same route. Likewise, if the composition comprises more than one active component, then those components may be administered by different routes. By way of example, the pharmaceutical composition of the invention may be formulated to be delivered using a minipump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by multiple routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile. For example, naltrexone may be coated with an enteric coating layer. The enteric coating layer material may be dispersed or dissolved in either water or in a suitable organic solvent. As enteric coating layer polymers, one or more, separately or in combination, of the following can be used; e.g., solutions or dispersions of methacrylic acid copolymers, cellulose acetate phthalate, cellulose acetate butyrate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). For environmental reasons, an aqueous coating process may be preferred. In such aqueous processes methacrylic acid copolymers are most preferred.

When appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For buccal or sublingual administration the compositions may be administered in the form of tablets or lozenges, which can be formulated in a conventional manner.

When the composition of the invention is to be administered parenterally, such administration includes one or more of: intravenously, intraarterially, intraperitoneally, intrathecally, intraventricularly, intraurethrally, intrasternally, intracranially, intramuscularly or subcutaneously administering the agent; and/or by using infusion techniques.

Pharmaceutical compositions of the invention can be administered parenterally, e.g., by infusion or injection. Pharmaceutical compositions suitable for injection or infusion may be in the form of a sterile aqueous solution, a dispersion or a sterile powder that contains the active ingredient, adjusted, if necessary, for preparation of such a sterile solution or dispersion suitable for infusion or injection. This preparation may optionally be encapsulated into liposomes. In all cases, the final preparation must be sterile, liquid, and stable under production and storage conditions. To improve storage stability, such preparations may also contain a preservative to prevent the growth of microorganisms. Prevention of the action of micro-organisms can be achieved by the addition of various antibacterial and antifungal agents, e.g., paraben, chlorobutanol, or ascorbic acid. In many cases isotonic substances are recommended, e.g., sugars, buffers and sodium chloride to assure osmotic pressure similar to those of body fluids, particularly blood. Prolonged absorption of such injectable mixtures can be achieved by introduction of absorption-delaying agents, such as aluminium monostearate or gelatin.

Dispersions can be prepared in a liquid carrier or intermediate, such as glycerin, liquid polyethylene glycols, triacetin oils, and mixtures thereof. The liquid carrier or intermediate can be a solvent or liquid dispersive medium that contains, for example, water, ethanol, a polyol (e.g., glycerol, propylene glycol or the like), vegetable oils, non-toxic glycerine esters and suitable mixtures thereof. Suitable flowability may be maintained, by generation of liposomes, administration of a suitable particle size in the case of dispersions, or by the addition of surfactants.

For parenteral administration, the compound is best used in the form of a sterile aqueous solution, which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Sterile injectable solutions can be prepared by mixing a compound of formula I with an appropriate solvent and one or more of the aforementioned carriers, followed by sterile filtering. In the case of sterile powders suitable for use in the preparation of sterile injectable solutions, preferable preparation methods include drying in vacuum and lyophilization, which provide powdery mixtures of the aldosterone receptor antagonists and desired excipients for subsequent preparation of sterile solutions.

The compound according to the invention may be formulated for use in human or veterinary medicine by injection (e.g., by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilizing, solubilizing and/or dispersing agents. Alternatively, the active ingredient may be in sterile powder form for reconstitution with a suitable vehicle, e.g., sterile, pyrogen-free water, before use.

Naltrexone can be administered (e.g., orally or topically) in the form of tablets, rapidly dissolving films, capsules, ovules, elixirs, solutions or suspensions, which may contain flavoring or coloring agents, for Immediate-, delayed-, modified-, sustained-, pulsed- or controlled-release applications.

Naltrexone may also be presented for human or veterinary use in a form suitable for oral or buccal administration, for example in the form of solutions, gels, syrups, mouth washes or suspensions, or a dry powder for constitution with water or other suitable vehicle before use, optionally with flavoring and coloring agents. Solid compositions such as tablets, rapidly dissolving films, capsules, lozenges, pastilles, pills, boluses, powder, pastes, granules, bullets or premix preparations may also be used. Solid and liquid compositions for oral use may be prepared according to methods well-known in the art. Such compositions may also contain one or more pharmaceutically acceptable carriers and excipients which may be in solid or liquid form.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate, stearic acid, glyceryl behenate and talc may be included.

The compositions may be administered orally, in the form of rapid or controlled release tablets, microparticles, mini tablets, capsules, sachets, and oral solutions or suspensions, or powders for the preparation thereof. In addition to the new solid-state forms of pantoprazole of the invention as the active substance, oral preparations may optionally include various standard pharmaceutical carriers and excipients, such as binders, fillers, buffers, lubricants, glidants, dyes, disintegrants, odourants, sweeteners, surfactants, mold release agents, antiadhesive agents and coatings. Some excipients may have multiple roles in the compositions, e.g., act as both binders and disintegrants.

Examples of pharmaceutically acceptable disintegrants for oral compositions include starch, pre-gelatinized starch, sodium starch glycolate, sodium carboxymethylcellulose, croscarmellose sodium, microcrystalline cellulose, alginates, resins, surfactants, effervescent compositions, aqueous aluminum silicates and cross-linked polyvinylpyrrolidone.

Examples of pharmaceutically acceptable binders for oral compositions include acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulphate.

Examples of pharmaceutically acceptable lubricants useful in the compositions of the invention include magnesium stearate, talc, polyethylene glycol, polymers of ethylene oxide, sodium lauryl sulphate, magnesium lauryl sulphate, sodium oleate, sodium stearyl fumarate, and colloidal silicon dioxide.

Examples of suitable pharmaceutically acceptable odourants for the oral compositions include synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include synthetic and natural dyes such as titanium dioxide, beta-carotene and extracts of grapefruit peel.

Examples of useful pharmaceutically acceptable coatings for the oral compositions, typically used to facilitate swallowing, modify the release properties, improve the appearance, and/or mask the taste of the compositions include hydroxypropylmethylcellulose, hydroxypropylcellulose and acrylate-methacrylate copolymers.

Examples of pharmaceutically acceptable sweeteners for the oral compositions include aspartame, saccharin, saccharin sodium, sodium cyclamate, xylitol, mannitol, sorbitol, lactose and sucrose.

Examples of pharmaceutically acceptable buffers include citric acid, sodium citrate, sodium bicarbonate, dibasic sodium phosphate, magnesium oxide, calcium carbonate and magnesium hydroxide.

Examples of pharmaceutically acceptable surfactants include sodium lauryl sulphate and polysorbates.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Naltrexone may also, for example, be formulated as suppositories e.g., containing conventional suppository bases for use in human or veterinary medicine or as pessaries e.g., containing conventional pessary bases.

Naltrexone may be formulated for topical administration, for use in human and veterinary medicine, in the form of ointments, creams, gels, hydrogels, lotions, solutions, shampoos, powders (including spray or dusting powders), pessaries, tampons, sprays, dips, aerosols, drops (e.g., eye ear or nose drops) or pour-ons.

For application topically to the skin, the agent of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax, sorbitan monostearate, a polyethylene glycol, liquid paraffin, polysorbate 60, cetyl esters wax, cetearyl alcohol, 2-octyldodecanol, benzyl alcohol, and water. Such compositions may also contain other pharmaceutically acceptable excipients, such as polymers, oils, liquid carriers, surfactants, buffers, preservatives, stabilizers, antioxidants, moisturizers, emollients, colourants, and odourants.

Examples of pharmaceutically acceptable polymers suitable for such topical compositions include acrylic polymers; cellulose derivatives, such as carboxymethylcellulose sodium, methylcellulose or hydroxypropylcellulose; natural polymers, such as alginates, tragacanth, pectin, xanthan and cytosan.

Examples of suitable pharmaceutically acceptable oils which are so useful include mineral oils, silicone oils, fatty acids, alcohols, and glycols.

Examples of suitable pharmaceutically acceptable liquid carriers include water, alcohols or glycols such as ethanol, isopropanol, propylene glycol, hexylene glycol, glycerol and polyethylene glycol, or mixtures thereof in which the pseudopolymorph is dissolved or dispersed, optionally with the addition of non-toxic anionic, cationic or non-ionic surfactants, and inorganic or organic buffers.

Examples of pharmaceutically acceptable preservatives include sodium benzoate, ascorbic acid, esters of p-hydroxybenzoic acid and various antibacterial and antifungal agents such as solvents, for example ethanol, propylene glycol, benzyl alcohol, chlorobutanol, quaternary ammonium salts, and parabens (such as methyl paraben, ethyl paraben and propyl paraben).

Examples of pharmaceutically acceptable stabilizers and antioxidants include ethylenediaminetetraacetic acid (EDTA), thiourea, tocopherol and butyl hydroxyanisole.

Examples of pharmaceutically acceptable moisturizers include glycerine, sorbitol, urea and polyethylene glycol.

Examples of pharmaceutically acceptable emollients include mineral oils, isopropyl myristate, and isopropyl palmitate.

The compounds may also be dermally or transdermally administered, for example, by use of a skin patch.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride.

As indicated, naltrexone can be administered intranasally or by inhalation and is conveniently delivered in the form of a dry powder inhaler or an aerosol spray presentation from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134AT) or 1,1,1,2,3,3,3-heptafluoropropane (HFA 227EA), carbon dioxide or other suitable gas. In the case of a pressurized aerosol, the dosage unit may be determined by providing a valve to deliver a metered amount. The pressurized container, pump, spray or nebulizer may contain a solution or suspension of the active compound, e.g., using a mixture of ethanol and the propellant as the solvent, which may additionally contain a lubricant, e.g., sorbitan trioleate.

Capsules and cartridges (made, for example, from gelatin) for use in an inhaler or insufflator may be formulated to contain a powder mix of the compound and a suitable powder base such as lactose or starch.

For topical administration by inhalation the compounds according to the invention may be delivered for use in human or veterinary medicine via a nebulizer.

The pharmaceutical compositions of the invention may contain from 0.01 to 99% weight per volume of the active material. For topical administration, for example, the composition will generally contain from 0.01-10%, more preferably 0.01-1% of the active material.

Naltrexone can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The pharmaceutical composition or unit dosage form of the invention may be administered according to a dosage and administration regimen defined by routine testing in the light of the guidelines given above in order to obtain optimal activity while minimizing toxicity or side effects for a particular patient. However, such fine tuning of the therapeutic regimen is routine in the light of the guidelines given herein.

The dosage of the active agents of the invention may vary according to a variety of factors such as underlying disease conditions, the individual's condition, weight, gender and age, and the mode of administration. An effective amount for treating a disorder can easily be determined by empirical methods known to those of ordinary skill in the art, for example by establishing a matrix of dosages and frequencies of administration and comparing a group of experimental units or subjects at each point in the matrix. The exact amount to be administered to a patient will vary depending on the state and severity of the disorder and the physical condition of the patient. A measurable amelioration of any symptom or parameter can be determined by a person skilled in the art or reported by the patient to the physician.

The pharmaceutical composition or unit dosage form may be administered in a single daily dose, or the total daily dosage may be administered in divided doses. In addition, co-administration or sequential administration of another compound for the treatment of the disorder may be desirable. To this purpose, the combined active principles are formulated into a simple dosage unit.

For combination treatment where the compounds are in separate dosage formulations, the compounds can be administered concurrently, or each can be administered at staggered intervals. For example, the compound of the invention may be administered in the morning and the additional antiviral compound may be administered in the evening, or vice versa. Additional compounds may be administered at specific intervals too. The order of administration will depend upon a variety of factors including age, weight, gender and medical condition of the patient; the severity and aetiology of the disorders to be treated, the route of administration, the renal and hepatic function of the patient, the treatment history of the patient, and the responsiveness of the patient. Determination of the order of administration may be fine-tuned and such fine-tuning is routine in the light of the guidelines given herein.

DETAILED DESCRIPTION OF THE INVENTION

In accordance with the present invention, an Immediate release naltrexone composition comprising between about 0.01 mg and about 10 mg of naltrexone may be administered to patients suffering from human immunodeficiency virus (HIV) acquired immune deficiency syndrome (AIDS, autoimmune disease, cancer, cardio vascular disease, inflammatory diseases, chronic inflammation, inflammatory bowel disease, Musculo-skeletal disorders, metabolic disorders and neurodegenerative diseases in the form of an Immediate release naltrexone tablets, rapidly dissolving films, liquids and cream, comprising from about 0.01 mg to about 10 mg of naltrexone in adults and about 0.05 to about 4.5 mg of naltrexone in children with suitable pharmaceutically-acceptable excipients, binders, sweeteners, coloring agents and other conventional additives.

Where high dose naltrexone and slow release naltrexone comprising between about 0.01 mg and about 10 mg of naltrexone and Immediate release naltrexone comprising between about 0.01 mg and about 10 mg of naltrexone share commonality" in categories of genes and are considered the same drug the difference in dosing and delivery method (Immediate release) difference in the overall response to the immune system.

There is a difference in the cell patterns of genes that are altered by the treatment of Immediate release naltrexone verses high does naltrexone and slow release low naltrexone comprises between about 0.01 mg and about 10 mg of naltrexone. The differences are important because Immediate release naltrexone comprising between about 0.01 and about 10 mg of naltrexone has as immunomodulator. Since Immediate release naltrexone blocks the opiate receptors only for a few hours before it is naturally excreted, what results is a rebound effect; in which both the production and utilization of met (5) enkelphine or opiate growth factor are increased. Once the Immediate release naltrexone has been metabolized, the elevated endorphins produced as a result of the rebound effect can now interact with the more-sensitive and more-plentiful receptors and assist in regulating cell growth and immunity. There is not rebound effect with either high dose naltrexone or slow release naltrexone and it is the rebound immunomodulatory effect that effects the treatment of treating patients suffering from human immunodeficiency virus (HIV) acquired immune deficiency syndrome (AIDS, autoimmune disease, opportunistic infections, cancer, inflammation, and neurodegenerative diseases The preferred method, an Immediate release naltrexone composition administered to patients in one daily dose which comprises about 0.01 to about 10 mg of naltrexone. The preferred time for dosing is after 8 PM to 11 PM bedtime but can be used in the morning as well.

The method of the present invention not only provides dramatic symptomatic relief for patients suffering from human immunodeficiency virus (HIV) acquired immune deficiency syndrome (AIDS, autoimmune disease, cancer, cardio vascular disease, inflammatory diseases, chronic inflammation, inflammatory bowel disease, Musculo-skeletal disorders, metabolic disorders and neurodegenerative diseases for example Alzheimer's, Asthma, Atopic Dermatitis Addison's disease Alopecia or Alopecia Areata, Antiphospholipid Syndrome, Autism, Autoimmune Hepatitis, Autoimmune hemolytic anemia, Autoimmune pancreatitis (AIP), Bullus pemphigoid, Celiac disease, Chronic bullous disease of childhood, Chronic sinusitis, Chronic inflammatory demyelinating Polyradiculoneuropathy (CIDP), Cictricial pemphigoid (CP), Depression, Complex Regional Pain Syndrome (CRPS), Crohn's Disease, Dermatitis herpetiformis (DH), Dermatomyositis, Evans syndrome, Ehlers Danlos Syndrome (EDS), Fatty liver, Graves' Disease Gullain-Barre syndrome, Hashimoto's, Inflammatory bowel diseases (colitis, enteritis and ileitis), HIV/AIDS, Insulin-dependent diabetes, Meniere's Disease, Mixed connective tissue disease or MCTD, Myasthenia, Multiple Sclerosis Multifocal motor neuropath, Neuromyotonia or Isaac's Palindromic Reflex Sympathetic Dystropy (RSD), Rheumatism, Pemphigus vulgaris causes, Pemphigus follaceus PF), Pemphigoid gestationis, Pernicious Anemia Paraneoplastic Pemphigus (PNP), Polymyalgia Rheumatica, Psoriasis, Psoriatic arthritis, Raynaud's phenomenon, Reactive Arthritis, Retinopathy, Rheumatoid arthritis, Sjogren's syndrome, Systemic lupus erythematosus, Systemic sclerosis (scleroderma) Thromboangiitis obliterans, Thyroiditis with hypothyroidism, Type I autoimmune polyglandular syndrome (PAS), Type II autoimmune polyglandular syndrome, Varicella-zoster virus, Wegener's granulomatosis Cancer: Adjunct to chemotherapy, breast, Hepatoblastoma, lymphoma, lymphadenopathy, ovarian, b-cell lymphoma, prostate, pancreatic cancer but has been found to reduce patient's systemic autoantibody level, increase production of increasing proliferation and functional activities of CD4+ T-cells and CD8+ T-cells which will play a role in anti-virus and anti-tumor activities; increasing maturation of dendritic cells which will initiate and intensify T-cell responses; increasing secretion of cytokines such as IL-2, TNF, IL-12 and IFN-γ which will amplify the T-cell response and mediate interaction among immune cells, including TRL-4 and TRL-9 forming a modulated and balanced immunity; increasing functions of macrophages, resulting in enhanced cellular immunity through secreting a set of cytokines; and increasing activity of NK cells which have the ability to kill cancer cells and virus-infected cells, lengthen telomerase slowing cell death potentially leading to a true remission in the course of the disease.

The following examples provide a detailed illustration of the method of the present invention. These examples are not intended to limit or restrict the scope of the invention in any way.

EXAMPLES

Human Immunodeficiency Virus (HIV) Clinical Trials

A single blind 90 day randomized bridging clinical trial was conducted in Nigeria to evaluate the impact of an Immediate release naltrexone composition comprising about 4.5 mg of naltrexone single oral dose on asymptomatic HIV+ adults undergoing antiretroviral (ART) treatment with CD4 counts below 360 average. The differences in CD4 count, CD4%, hemoglobin, viral load, interferon alpha, and standard chemistry panel were measured between treated versus non-treated groups four times throughout the study. The results showed an improvement in CD4 count in the treatment group was 53 that were significantly greater than the control group (54 subjects) at 3 months with an increase of 44%. Improvement in CD4% in the treatment group was observed throughout treatment, and the increases were statistically significant. In addition to the changes in CD4 count patients saw an increase in BMI, reduction in opportunistic infections. These data presented herein on patients who have been placed on an Immediate release naltrexone composition comprising between about 0.01 and about 10 mg of naltrexone who have HIV/AIDS show that it has the ability to be an effective immune-enhancing agent specifically in this disease by increasing or stabilizing a patient's CD4 count or by providing a decline in IFN-α levels and viral loads. When used alone, it appears to slow and/or stop the progression of the disease. When used in combination with antivirals, an Immediate release naltrexone composition comprising between about 0.01 mg and about 10 mg appears to accelerate immune system healing and increase CD4 levels.

A single blind nine-month randomized clinical trial was conducted in Mali to evaluate the impact of an Immediate release naltrexone composition comprising about 3 mg of naltrexone on asymptomatic HIV+ adults undergoing antiretroviral (ART) treatment with CD4 counts below 350 cell/mm3. The differences in CD4 count, CD4%, hemoglobin, viral load, interferon alpha, and standard chemistry panel were measured between treated versus non-treated groups five times throughout the study. The results showed an improvement in CD4 count in the treatment group (51 subjects) that was significantly greater than the control group (49 subjects) at 6 months (p=0.041) and marginally at 9 months (p=0.067). Improvement in CD4% in the treatment group was observed throughout treatment, but these increases were not statistically significant (Traore A K. et al., September 2011). The results were effected by the fact the product was compounded and was dosed at 3 mg rather then 4.5 mg Naltrexone as an adjunct therapy with HIV/AIDS patients. HIV 50 patients in Africa in conjunction with standard of care, where ART extends live it does not fully restore health. HIV disease is associated with a new constellation of problems, generally referred to as "non-AIDS morbidity", and, in the popular press, "premature aging. IV replication are at risk for developing a number of non-AIDS conditions, including cardiovascular disease, cancer, kidney disease, liver disease, osteopenia/osteoporosis and neurocognitive disease (collectively referred to as "serious non-AIDS events"). Malignancies associated with infections such as human papilloma virus (including uro-genital and head and neck cancers), Epstein Barr Virus (including Hodgkins disease), and hepatitis B and C (hepatocellular carcinoma), are also relatively common in HIV-infected adult. A rapidly growing and remarkably consistent evidence base indicates that many markers of inflammation are higher in antiretroviral-treated adults than in age-matched uninfected individuals[30, 31]. Subtle elevations in many of these biomarkers are associated with dramatic increases in the risk of subsequent disease, including all-cause mortality For example, as compared to a well-matched uninfected population, treated HIV-infected adults have approximately 50 to 100% higher levels of the inflammatory cytokine interleukin-6 (IL-6)[32]. Patients taking Naltrexone showed: Secreased inflammatory cytokine and a shift from Th1 (pro-inflammatory) to Th2 (anti-inflammatory) and effect on Treated with immunotherapies/cytokine antibodies (TNF, IL-2, IL-10) as well Affects microglia—macrophages/1$^{st}$ line of immune defense in CNS; normally quiescent Cell death, inflammation, infection→Activated microglia→increase in proinflammatory cytokines, excitatory amino acids, and nitric oxide (NO) Increased NFκB→additional proinflammatory cytokines that act on neurons to create pain, fatigue, etc. Risk factors for impaired CD4 T-cell recovery include low pre-treatment CD4+ T cell count nadir, co-infection with other viruses such as hepatitis C, older age, and perhaps viral factors (24). Suboptimal treatment-mediated CD4+ T cell outcomes likely have clinical consequences given the consistent association between CD4+ T cell counts during ART and elevated risk of many co-morbidities (e.g., heart disease, cancer) and all-cause mortality. Chronic signaling through the interferon-alpha pathway may contribute to this inflammatory disease[32], as can the impact of virus production/entry (without productive infection) on pyroptosis, which is a highly inflammatory process that can cause death of affected and neighboring cells. The frequency of activated T cells remains elevated during chronic treatment and appears related to size of the HIV reservoir and pace of immune reconstitution although the effect of this marker in predicting overall morbidity and mortality is not as strong as some of the innate immune system inflammatory markers[37].

Patients saw a reduction in opportunistic infection and a higher quality of live over the long term. We believe that long term monitoring of patients will show a reduction in non-AIDS morbidity.

A single blind nine-month randomized clinical trial was conducted in Mali to evaluate the impact of an Immediate release naltrexone composition comprising between about 0.01 mg and about 10 mg of naltrexone on asymptomatic HIV+ adults undergoing antiretroviral (ART) treatment with CD4 counts below 350 cell/mm3. The differences in CD4 count, CD4%, hemoglobin, viral load, interferon alpha, and standard chemistry panel were measured between treated versus non-treated groups five times throughout the study. The results showed an improvement in CD4 count in the treatment group (51 subjects) that was significantly greater than the control group (49 subjects) at 6 months (p=0.041) and marginally at 9 months (p=0.067). Improvement in CD4% in the treatment group was observed throughout treatment, but these increases were not statistically significant (Traore A K. et al., September 2011). The results on this trial were not an effective because the Immediate release naltrexone used was compounded and was only 3 mg rather then 4.5 mg which has been shown to be the most effective dose.

A 12-week, placebo-controlled trial of IMMEDIATE RELEASE NALTREXONE (LDN) from 1985-1986 in 38 patients with AIDS. Patients were administered 3.0 mg IMMEDIATE RELEASE NALTREXONE (LDN) daily at bedtime. Patients who participated in this trial showed a significant difference in the incidence of opportunistic infections with 5 out of 16 patients (31%) on placebo developing opportunistic infections in comparison to 0 of the 22 patients in the Immediate release naltrexone (LDN) group. Other difference between placebo and Immediate release naltrexone (LDN) treated patients included: lymphocyte mitogen responses declined on placebo and not on Immediate release naltrexone; pathologically elevated levels of acid-labile alpha interferon declined significantly in the patients on Immediate release naltrexone and not in those patients on placebo (Bihari et al., September 1996).

A study of 55 patients two are trial one with Two Groups One on Epivir and AZT and one group on Epiviver and AZT neither group had taken AZT before the study. The Glaxo patients on Epivir and AZT experienced an average rise of 40 CD4's at 6 months. This represents an 11.3% increase. The patients on Epivir, AZT and Immediate release 4.5 mg naltrexone experienced an average rise of 106 CD4's at 6 months, representing a 128% increase. All 19 of the patients in the naltrexone group had increases of at least 30%. In addition, there was, in all but one, a significant increase in energy, appetite and mood. In several underweight patients there were weight gains of 10 to 50 pounds in the first 2 months with no opportunistic infection. New England Journal of Medicine of Dec. 21, 1995 (vol. 333, number 25, pg. 1662) reported by an investigator working for Glaxo.

Cancer 89 patients Hematologic Cancer Patients This was a randomized controlled trial assessing quality of life in patients with hematologic malignancies from a single institute in Hamedan. Patients were allocated into two study arms and in addition to their routine treatment received either daily naltrexone 3 mg capsules (treatment group) or 3 mg starch (placebo group) and were followed up for 5 months. Quality of life was measured using the EORTC QLQ-C30 in four points in time (at admission, 1, 3 and 5 months follow-up).

Data were analyzed to compare quality of life in two groups. In total, 89 patients were studied (45 in treatment group and 44 in placebo group). There were no significant differences between two groups either in demographic and clinical characteristics or in baseline quality of life scores.

However, at 1 month, 3 and 5-month follow-up assessments significant differences were observed. In one month follow-up two groups were significantly different in social functioning (p<0.05) indicating a better condition in the treatment group. In the 3-month follow-up, social functioning, role functioning, nausea and vomiting and appetite loss were better in the treatment group (all p-values<0.05). In the 5-month follow-up, physical functioning, social functioning, role functioning, global quality of life, nausea and vomiting and appetite loss were significantly better in the naltrexone group. Lodonal or Low dose naltrexone is an effective drug in improving quality of life in patients with hematologic cancers undergoing treatment.

Twenty-nine of the patients had Kaposi's sarcoma (K.S.), six previously had a major opportunistic infection (O.I.) and three had both O.I. and K.S. The mean time of the 38 patients from AIDS diagnosis to admission into the study was 7.6 months. Thirty-one of the 38 patients had a baseline absolute T4 count of less than 300/ml. Immediate release naltrexone was administered at a dose of 1.75 mg nightly at bedtime. During the 3-month double-blind period, a significant drop in elevated levels of serum alpha interferon (IFN-α) was observed in those patients receiving LDN compared with the placebo patients (p<0.01). After completion of this double blind period, all of the 38 patients were placed on Immediate release naltrexone. Twenty-three of the 38 patients showed a marked decline in IFN-α levels (from means of 144.9 IU. to 11.0 IU. over a 12-month period) while the remaining 15 did not show such a decline. Nineteen of the 23 (83%) who showed a decline in IFN-α survived while only 2 of the 15 (13%) who did not show such a decline survived (p<0.01). No side effects were noted during the conduct of this trial.

This study aimed to investigate its effect on hematologic cancer patients. This was a randomized controlled trial assessing quality of life in patients with hematologic malignancies from a single institute. Patients were allocated into two study arms and in addition to their routine treatment received either daily Immediate release naltrexone 3 mg capsules (treatment group) or 3 mg starch (placebo group) and were followed up for 5 months. Quality of life was measured using the EORTC QLQ-C30 in four points in time (at admission, 1, 3 and 5 months follow-up). Data were analyzed to compare quality of life in two groups. Totally, 89 patients were studied (45 in treatment group and 44 in placebo group). There were no significant differences between two groups either in demographic and clinical characteristics or in baseline quality of life scores. However, at 1 month, 3 and 5-month follow-up assessments significant differences were observed. In one month follow-up two groups were significantly different in social functioning (p<0.05) indicating a better condition in the treatment group. In the 3-month follow-up, social functioning, role functioning, nausea and vomiting and appetite loss were better in the treatment group (all p-values<0.05). In the 5-month follow-up, physical functioning, social functioning, role functioning, global quality of life, nausea and vomiting and appetite loss were significantly better in the Immediate release naltrexone group. Immediate release naltrexone between 0.01 to 10 mg is an effective drug in improving quality of life in patients with hematologic cancers. Most importantly, there were no changes in the blood laboratory tests with Immediate release naltrexone. Compared to standard chemotherapy that reduces the blood count from bone marrow toxicity, white blood cell, red blood cell and plate count remained stable with Immediate release naltrexone.

Treatment of advanced pancreatic cancer with Opioid Growth Factor in 24 patients Clinical benefit response was experienced by 53% of OGF-treated patients compared to historical controls of 23.8% and 4.8% for gemcitabine and 5-fluorouracil (5-FU), respectively. Of the subjects surviving more than eight weeks, 62% showed either a decrease or stabilization in tumor size by computed tomography. The median survival time for OGF-treated patients was three times that of untreated patients (65.5 versus 21 days, p<0.001). No adverse effects on hematologic or chemistry parameters were noted, and quality of life surveys suggested improvement with OGF. This trial shows that Immediate release naltrexone can slow or cause cell death.

A 46-year-old man diagnosed in October 2002, with poorly differentiated adenocarcinoma of the pancreas with metastases to the liver, began intravenous treatment with α-lipoic acid (ALA) 300 to 600 mg two times per week, 4.5 mg Immediate release naltrexone (LDN) once per day at bedtime, oral ALA (600 mg/day), selenium (200 μg two times per day), and silymarin (300 mg four times a day), including a strict dietary regimen along with a stress-reduction and exercise program. The average length of survival after diagnosis of pancreatic cancer ranges from 3 to 6 months; however this patient, at the time this article was written in 2006 showed comparatively stable disease for more than a 3-year period and an improved quality of life (Berkson et al., 2006).

A 61-year old man was diagnosed with biopsy-proven Follicular Lymphoma (FL). His initial physical examination and PET/CT scan showed multiple large, metabolically active, pathologic lymph nodes. After 6 months of receiving Immediate release naltrexone (LDN) daily in the evening, in addition to a prescribed healthy diet, a nutritional supplement regimen, and intravenous α-lipoic acid (ALA). This patient however, did not remain compliant with the diet, the nutritional supplement, or the ALA. Thus the achievement of clinical and radiological remission was deemed to be due to the IMMEDIATE RELEASE NALTREXONE (LDN) alone. In 2007 when this report was published, per telephone communication from the patient's wife, the patient remains asymptomatic from his disease, 1 year after his last CT/PET imaging (Berkson et al., 2007).

Three patients presented to the same clinic and were all treated with the same ALA+ Immediate release naltrexone (LDN) protocol. The patients presented with the following diseases and had the following outcomes: Adenocarcinoma of the pancreas with metastases to the liver. This patient is alive and well 39 months after presentation of disease and initiation of ALA+ Immediate release naltrexone (LDN) therapy. Adenocarcinoma of the pancreas with metastases to the liver, presented with the same diagnosis as the above patient. After 5 months of ALA+ Immediate release naltrexone (LDN) therapy, a PET scan demonstrated no evidence of disease.

Pancreatic cancer with liver and retroperitoneal metastases, with a history of B-cell lymphoma and prostate adenocarcinoma. After 4 months of ALA+ Immediate release naltrexone (LDN) therapy his PET scan demonstrated no signs of cancer (Berkson et al., 2009).

Two Case Studies: Hepatoblastoma is the most common liver malignancy in children, typically diagnosed before age 2. The survival rate for hepatoblastoma has increased dramatically in the last 30 years, but the typical chemotherapeutic agents used for treatment are associated with significant toxicity. In this report, the authors present two cases of hepatoblastoma treated with surgical resection and a novel biotherapeutic regimen that included opioid growth factor (OGF). Case #1 is an infant diagnosed with a large mass on prenatal ultrasound. After subsequent diagnosis of hepatoblastoma, she was treated with one course of neoadjuvant chemotherapy at approximately 1 week of age. Following significant complications from the chemotherapy (neutropenic fever, pneumonia and sepsis), the patient's parents declined further chemotherapy, and the infant was treated with surgical resection and opioid growth factor (OGF)/Immediate release naltrexone. She is currently at close to 10 years disease-free survival. Case #2 is a child diagnosed with a liver mass on ultrasound at 20 months of age, later biopsy-proven to represent hepatoblastoma. Due to existing co-morbidities including autosomal recessive polycystic kidney disease and hypertension, and indications from the biopsy that the tumor might be insensitive to chemotherapy, the parents elected not to proceed with neoadjuvant chemotherapy. The patient was treated with surgical resection and OGF/IMMEDIATE RELEASE NALTREXONE (LDN), and is currently at more than 5 years disease-free survival. This case series highlights the need for less toxic treatment options than conventional chemotherapy. Modulation of the OGF-OGF receptor axis represents a *promising safe and therapeutic avenue for effective treatment of hepatoblastoma*. Rogosnitzky M, Finegold M J, McLaughlin P J, Zagon I S. *Invest New Drugs*. 2013 August; 31(4): 1066-70.

85-year-old man diagnosed with stage 3-stomach cancer prognosis 6 months to live on Mar. 15, 2007 and started Immediate release naltrexone 4.5 mg on Mar. 28, 2007. In addition to Immediate release naltrexone patients received chemotherapy and kidney stents inserted. Immediate release naltrexone was started after two rounds of chemotherapy in September 2007 patient had a CT scan, that showed tumors shrunk in half and removed the kidney stents. In December of 2007 patients was determined to be in remission and stable. In March 2008 another CT scan was done and tumors had shrunk in half, and a third scan was done in March of 2009 and tumors were stable. Patients from 2007 through 2009 continued on 4.5 mg of Immediate release naltrexone.

75 year old woman diagnosed with stage 4 pleural mesothelioma in December of 2008 and patients after consult with two other doctors it was determined due to the state of the diseases and other health issues to watch the tumors and not do chemotherapy. Prognosis was 6 to 12 months. Patient started 4.5 mg nightly and received on other treatment but did change diet. Two CAT scans February 2009 and 2010 both showed no measurable growth of tumors. Immediate release naltrexone between 0.01 mg and 10 mg has been shown to stabilize or show the growth of tumors.

A 69 year old man diagnosed with stage 4-colon cancer, 2007 which had spread to his lungs and liver, they removed 40% of his colon and began a round of chemotherapy and three surgeries removed 40% of his colon, half is his right lung and 75% of his liver. During the next 18 months received 47 weeks of chemotherapy (a combination of 4 chemo drugs at once). Was going to stop chemotherapy due to toxic side-effects but started IMMEDIATE RELEASE NALTREXONE in June of 2007 he started 4.5 mg nightly of IMMEDIATE RELEASE NALTREXONE immediately and was able to complete the entire protocol without any major side effects at all. Patient had scans every six months and continued cancer free until June of 2015 when they found a small growth in his right lung which they removed with no need for chemotherapy or radiation.

87 years old male was diagnosed with stage 3 prostate cancer which he was originally treated for 5 years before began 3 rounds of Docetaxel (Taxotere®). He was prescribed 4.5 mg of IMMEDIATE RELEASE NALTREXONE which he took nightly and has continued with since the completion of the protocol. Patient was able to withstand the chemotherapy and his blood work stayed stable throughout the protocol, and maintained his weight, and overall quality of life was much better.

Parkinson Disease

A eight-week clinical study in which 48 PD patients diagnosed with one or more ICDs that developed during PD and in the context of dopamine agonist (DA) treatment will receive either naltrexone or placebo treatment in a blinded fashion. Recruitment will be such that all four common ICDs in PD (compulsive gambling, buying, sexual behavior and eating) are equally represented. Patients will be seen every other week during the course of the study, and treatment response and tolerability will be assessed at each visit.

The results of this study were negative for the efficacy of Immediate release naltrexone at 4.5 mg for the treatment of impulse controls disorders (such as compulsive gambling, buying, sexual behavior and eating) in Parkinson's disease (PD) using a clinician rating of general improvement, which was the primary outcome measure for the study. However, using a patient-completed, PD-specific assessment of impulse control disorder symptom severity, naltrexone treatment was associated with a significant decrease in symptoms compared with placebo treatment. The results of this preliminary study support further research with naltrexone for the treatment of these disorders in PD.

A 63 year old woman diagnosed with Parkinson disease in October 2008 during the next three years doctors prescribed Sinemet, Requip caused major side effects, falling asleep while driving, and Symmetrel had to stop work, while they helped offer relief from her symptoms. In June of 2011 patient started on 4.5 mg of IMMEDIATE RELEASE NALTREXONE and over the next 6 month was able to titrate off all other medications and the majority of patient's symptoms have subsided.

A 72 year old male diagnosed with Parkinson Disease in October 2009 suffered brain fog, shaking on right hand, very tired started 3 mg of IMMEDIATE RELEASE NALTREXONE in August of 2013 as none of the standard treatments were not helping or the side effects were not acceptable. Patient continues on IMMEDIATE RELEASE NALTREXONE today as his only treatment patients confirms brain fog gone and shaking is less.

A 66 year old male diagnosed with Parkinson Disease in November of 2011, patient suffered from hand/arm tremors, jaw/tongue tremors, memory impairment, lack of cognitive function, sleep disorder mask like appearance, patient started on 1.5 mg of IMMEDIATE RELEASE NALTREXONE titrating up to 3 mg. Major improvement within first 2 weeks at 1.5 mg jaw/tongue tremors stopped and by 2nd month at 3 mg patients sats mental function restore, hand/arm tremors have lessened and patient has returned to work patient takes on PD medications and continues on IMMEDIATE RELEASE NALTREXONE.

Autism 155 children participated in 10 studies; 27 received placebo. Of the 128 that received naltrexone 98 (77%) showed statistically significant improvement in symptoms of irritability and hyperactivity. Side effects were mild and the drug was generally well tolerated.

Randomized, double blind, placebo-controlled study with Immediate release naltrexone in the treatment of autism. Eight of 13 subjects improved in two or more settings. Changes in parent measures (CGI, Conners Impulsivity-Hyperactivity Factor, and SE-Restlessness) and Teacher CGI achieved statistical significance. Teacher SE-Restlessness and initiation of communication in the clinic showed a trend toward improvement. Actometer readings improved in two children who were very active at baseline.

Opioid-immune interactions in autism: behavioral and immunological assessment during a double-blind treatment with naltrexone. The behavioral improvement was accompanied by alterations in the distribution of the major lymphocyte subsets, with a significant increase of the T-helper-inducers (CD4+CD8−) and a significant reduction of the T-cytotoxic-suppressor (CD4−CD8+) resulting in a normalization of the CD4/CD8 ratio. Changes in natural killer cells and activity were inversely related to plasma beta-endorphin levels. It is suggested that the mechanisms underlying opioid-immune interactions are altered in this population of autistic children and that an immunological screening may have prognostic value for the pharmacological therapy with opiate.

9 year old boy diagnosed with Autism & ADHD in June of 2007 no eye contact and chronic stomach pain started IMMEDIATE RELEASE NALTREXONE in 2009 started at 0.1 mg for 2 weeks then 2 mg 2 weeks 3 mg more TICS for month as on Ritaline, Risperdal, Dexamine, today only takes IMMEDIATE RELEASE NALTREXONE good eye contact and almost on pain.

4 year old girl diagnosed with Autism in 2008 was continually sick started IMMEDIATE RELEASE NALTREXONE in October 2009 side effect a little constipation 5 ml at bedtime celxia and have continued celxia plus IMMEDIATE RELEASE NALTREXONE has not been sick since starting IMMEDIATE RELEASE NALTREXONE and language skills have improved. This is important as many children with Autism suffer from IBS.

5 year old boy diagnosed with Autism in 2007 with autoimmune problems, very low NK activity, started IMMEDIATE RELEASE NALTREXONE 3 mg in August of 2009, hyperactivity increased for the first three weeks. Over the next months social behaviors skyrocketed after IMMEDIATE RELEASE NALTREXONE. Started requesting "play dates" with friends when that had never been a desire before. Developed real friendships after starting IMMEDIATE RELEASE NALTREXONE in addition to IMMEDIATE RELEASE NALTREXONE he takes Nystatin, Fluconazole and supplements continues taking IMMEDIATE RELEASE NALTREXONE today Autoimmune Hepatitis Hepatic Methionine-enkephalin may interfere with response to antiviral therapy in chronic hepatitis sought to investigate the expression of the immunoreactivities of Met-enkephalin and of the δ-opioid receptor 1 (DOR1), to which Met-enkephalin binds, preferentially, in liver samples from 23 patients with chronic hepatitis C who had undergone antiviral therapy. Twelve patients obtained a sustained virological response, and 11 patients were relapsers after or nonresponders to treatment. Among the 12 patients with sustained virological response, one patient (8.3%) expressed MEIR and another one expressed DOR1 immunoreactivity (8.3%), whereas none of the patients expressed both immunoreactivities. Among the group of nonresponders/relapsers, one patient expressed MEIR (9%), two patients expressed DOR1 immunoreactivity (18.2%), and seven patients expressed both (63.6%). The difference between responders and nonresponders in the expression of both immunoreactivities was significantly different ($P<0.001$).

A 63 year old woman diagnosed January of 2012 with Hepatitis C and Diabetes started taking IMMEDIATE RELEASE NALTREXONE January 2013 4 mg once a day in the morning. Was being controlled by Prednisone but was having increasing side effects, and decided to try IMMEDIATE RELEASE NALTREXONE. Patient no longer takes prednisone or other immunosupression drugs, continues to take 4 mg in morning A 63-year-old female diagnosed with Autoimmune Hepatitis—Type 1 November of 2008 was taking Prednisone, Azathioprine, and 6MP, Cellcept, Budesonide. Patients was having Liver function tests monthly and they were elevated and rising monthly. Patient had vivid dreams and mild indigestion in the first two weeks. Patients for the first year had monthly blood tests hepatitis is under control with only 4.5 mg IMMEDIATE RELEASE NALTREXONE nightly A 57 year old male diagnosed with Hepatitis C October 2002 patients suffered from fatty liver, chronic hepatitis C, elevated liver enzymes, sever fatigue, IBD and Fibromyalgia and was treated with a number of different immunosupression drugs including prednisone, Patient started IMMEDIATE RELEASE NALTREXONE in February of 2009 and stopped all other medication and recent ultrasound shown No fatty liver, Liver enzymes dropped to normal, HCV viral load dropped from over a million in January 2009 to 49,000 in May 2009. In May 2010, it had dropped down to 11.400. Patient continues to be stable has more energy, IBS is no longer a problem and fibromyalgia is greatly improved.

A 6 year old girl diagnosed with Hepatitis B failed standard treatment started 1 mg Immediate release IMMEDIATE RELEASE NALTREXONE within one month viral load decreased from 59.2 million to 53,000, ALT/AST decreased to normal. Within 7 months Sero-conversion to negative antigens and positive antibodies, Viral load 551 additional benefits included resolutions of eczema.

A 52 year old man diagnosed with Hepatitis C & stage 4 cirrhosis of the liver after one year of intensive alpha lipoic acid, glutathione therapy, liver enzyme levels normal, Viral load still high and patient on transplant list Started Immediate release IMMEDIATE RELEASE NALTREXONE 4.5 mg March of 2011 Viral load dropped from 24.4 million to 11.9 million by May of 2011 by August of 2011 viral load dropped to 8.3 million and has continued to drop through 2012

Blepharitis 62-year-old male diagnosed with blepharitis at age 45 was treated with various drugs including Antibiotic ointment and Restasi. Patient began treatment with 3 mg of IMMEDIATE RELEASE NALTREXONE February of 2014 and realized that his blepharitis has been cured for the first time in many years.

Complex Regional Pain Syndrome (CRPS)

A 48 year-old male veteran sustained an injury to his right leg in 2006. While undergoing aqua-therapy, he injured his right great toe, which subsequently became infected. Following drainage of an abscess and removal of the great toe's nail, the patient developed the following CRPS symptoms in his right lower extremity: swelling, allodynia (pain to normal touch), color change, temperature change, and some weakness. By 2007, the patient developed moderate CRPS symptoms in his upper extremities. In 2008, he developed blisters and skin ulceration in his right lower extremity (FIG. 1). At this time, the patient was being treated with opioids, pregabalin, and duloxetine. By 2009, the patient's pain had become severe enough that he could not ambulate without assistance. He developed muscle spasms in the right upper extremity. In 2010, he underwent a cardiac bypass surgery for coronary artery disease. His CRPS symptoms became widespread after this surgery, spreading to his upper chest, upper arms, and forearms. In 2011, the patient developed significant dystonic spasms to both upper extremities, resulting in hyperextension of his fingers. From 2008 to 2012, the patient underwent multiple treatments with anticonvulsants, antidepressants, physical therapy, psychotherapy, topical and systemic analgesics, including but not limited to opioids. The patient also currently has diabetes mellitus type II, hypertension, hyperlipidemia, as well as coronary artery disease.

In August of 2011, the patient began low-dose intravenous ketamine infusions. He reported a good initial response, but the relief was not sustained. He continued to have ketamine booster infusions at intervals of 4 to 6 weeks. Although the patient engaged in aggressive physical therapy during this time, his maximum interval of relief from pain following a given ketamine infusion decreased to an interval of 3 weeks. In January 2012, his use of the opioid oxycodone was changed to tapentadol. This narcotic was removed for 1 week prior to starting low-dose naltrexone, which was started and maintained at 4.5 mg per day (1 dose at night). Additional medications included: metformin, tramadol, valsartan, cloazepate, simvastatin, fish oil, and vitamin C. Immediately before IMMEDIATE RELEASE NALTREXONE treatment, the patient had patchy areas of allodynia to the medial and dorsal aspect of his right foot, extensive areas of dysesthesia in his right lower extremity below the knee and heel of his foot, as well as bilaterally dysesthesia in the upper extremities. There were significant color and temperature changes in the right foot compared to the left foot, as well as pitting edema in the right foot. A triple-phase bone scan revealed significant reuptake in the right foot, characteristic of CRPS. By March of 2012, the patient's requirements for the lower dose intravenous ketamine infusions were not as frequent (6 week intervals, pain spikes not as high). The patient recovered from CRPS flares more quickly, felt more energetic, and tolerated pain better. He became physically more active, and his sleep improved significantly. Within 2 months after starting IMMEDIATE RELEASE NALTREXONE, the patient's dystonic spasms discontinued, although he still had moderate pain in both upper extremities. The patient was able to walk without a cane (FIG. 2b), which he had used continuously since 2006. His pain was an average of 8 to 10 on the Numeric Rating Scale (NRS) before starting IMMEDIATE RELEASE NAL- TREXONE. It dropped down to an average of 5 to 6 on the NRS after starting IMMEDIATE RELEASE NALTREXONE. After IMMEDIATE RELEASE NALTREXONE therapy, the patient's pain symptoms have reduced in severity, but not in their distribution. His current mood state is good. No side effects of IMMEDIATE RELEASE NALTREXONE were noted.

A female patient, currently 12 years old, has a genetic disorder, Ehlers-Danlos Syndrome (EDS) hypermobility type 1, dysautonomia, non-epileptic seizures, chronic gastritis, mitochondrial dysfunction, asthma, vision loss, thyroid tumor and anti-cardiolipin antibodies. As a result of her EDS, the patient has had repeated dislocations of her right shoulder, as well as her right ankle. The patient first developed CRPS in her lower right extremity in 2008. In 2009, the patient developed dystonic muscle spasms in the upper extremities, which were interpreted by her physicians as evidence of a conversion disorder. The patient was first seen by one of us (PC) in February of 2011. Her symptoms of CRPS included color change, increased temperature in the right foot (90° C.) versus (82° C.) in the left foot, allodynia over the dorsum of right foot, and patchy areas of dysesthesia over her right leg. She also had areas of allodynia and dysesthesia in the left lower extremity and both upper extremities, as well as distorted nails on the right foot. When first seen, the patient's medications were levetiracetam, midodrine, baclofen, trazodone, diphenhydramine, lansoprazole, budesonide, levalbuterol, L-Carnitine, coenzyme Q10, vitamin D, vitamin C, magnesium, and vitamin B complex. She rated her pain on a NRS (Numerical Rating Scale) as 8/10 at its lowest and 10/10 at its worst. In early 2011, the patient experienced a subluxation of her right ankle. The lower right leg and ankle subsequently developed fixed dystonia, with plantar flexion and varus. Fixed dystonia, allodynia, and vasomotor abnormalities in the right lower extremity of a CRPS patient (panel a) remitted following treatment with a low-dose naltrexone. No symptoms and signs of CRPS after IMMEDIATE RELEASE NALTREXONE treatment. Two months after surgical reinforcement of the right ankle for Ehlers-Danlos Syndrome (EDS) In June 2011, the patient was started on low dose naltrexone (IMMEDIATE RELEASE NALTREXONE) of 3 mg once a day and ketamine troches (sublingual) 10 mg on as needed basis. The IMMEDIATE RELEASE NALTREXONE was increased to 4.5 mg per day, 4 weeks after starting it. IMMEDIATE RELEASE NALTREXONE was started as a lower dose to gauge tolerability. She tolerated the IMMEDIATE RELEASE NALTREXONE very well with no reports of adverse effects. Her pain scores dropped from NRS (7-10)/10, to (3-5)/10. She also reported a decrease in allodynia, as well as a decrease in sensitivity to touch and temperature change. There was no effect on the dystonia. Two months after starting IMMEDIATE RELEASE NALTREXONE, she underwent 400 units of botulinum toxin, injections to the right gastrocnemius group of muscles with minimal relief of her dystonia. The right lower extremity was placed in an above knee cast for 6 weeks. Several weeks after the cast was removed, the patient subluxated her right ankle again. She underwent a 400 units injection of botulinum toxin, and a cast was applied again. The patient used ketamine troches (10 mg) for 3 weeks after the IMMEDIATE RELEASE NALTREXONE was started, as needed for pain. She was taking ketamine troches on as needed basis for acute flare-ups of her CRPS pain. This was limited to no more than 30 mg of ketamine troches per day. The patient progressively reduced her use of ketamine troches 3 weeks after starting IMMEDIATE RELEASE NALTREXONE, and by 8 weeks was taking them rarely. In December of 2011, she underwent percutaneous pinning of the right ankle to stabilize the joint. The pins were removed 6 weeks later and the ankle joint subluxated again. In February of 2012, the patient underwent reinforcement to the right ankle with cadaver ligaments. She continued to be on low dose naltrexone during this time, except for 4 perioperative days, during which the IMMEDIATE RELEASE NALTREXONE was discontinued. As per institutional protocol, IMMEDIATE RELEASE NALTREXONE was stopped for 24 h before surgery. After surgery, she was given oral opioids (hydrocodone with acetaminophen) for 1 week. The oral opioids were then discontinued, and IMMEDIATE RELEASE NALTREXONE treatment was resumed 24 h, after her last dose of opioid. The patient noticed a decrease in her post-operative pain, ranging from (4-6)/10, 3 weeks after resuming IMMEDIATE RELEASE NALTREXONE. Skin discoloration and allodynia could not be assessed after the surgery because her leg was in a cast. At the time of cast removal, the patient's lower leg and ankle had a normal range of motion, indicating a remission of the leg's fixed dystonia (FIG. 3b). The leg had a slight red color at the time of cast removal, but no allodynia. Ten months after surgery, the patient's gait was normal. Remarkably, the patient did not experience any spread of her CRPS, despite undergoing multiple invasive procedures, including surgery. One of the known triggers for a CRPS flare-up, or spread of CRPS symptoms, is trauma (Schwartzman et al. 2009; van Rijn et al. 2011). The patient still has a chronic shoulder dislocation, associated with her EDS. However, her CRPS symptoms have resolved completely. The patient has been maintained on IMMEDIATE RELEASE NALTREXONE for 18 months. No side effects of IMMEDIATE RELEASE NALTREXONE have been noted.

Crohn's Disease

A pilot clinical trial was conducted in children with moderate to severe Crohn's disease. Fourteen subjects with a mean age of 12.3 years (range, 8 to 17 y) were enrolled. Children were randomized to placebo or Immediate release naltrexone (0.1 mg/kg) orally for 8 weeks followed by open-labeled treatment with 8 additional weeks of naltrexone. Safety and toxicity were monitored by physical examinations and blood chemistries. Clinical activity was assessed by the Pediatric Crohn's Disease Activity Index (PCDAI) and Quality of life was monitored by the Impact III survey. Oral Immediate release naltrexone was well tolerated without any serious adverse events in children with moderate to severe Crohn's disease. PCDAI scores significantly decreased from pretreatment values (34.2±3.3) with an 8-week course of naltrexone therapy (21.7±3.9) (P=0.005). Twenty-five percent of those treated with naltrexone were considered in remission (score≤10) and 67% had improved with mild disease activity (decrease in PCDAI score by at least 10 points) at the end of the study. Systemic and social quality of life improved with naltrexone treatment (P=0.035).

Eligible subjects with histologically and endoscopically confirmed active Crohn's disease activity index (CDAI) score of 220-450 were enrolled in a study using 4.5 mg naltrexone/day. Infliximab was not allowed for a minimum of 8 weeks prior to study initiation. Other therapy for Crohn's disease that was at a stable dose for 4 weeks prior to enrollment was continued at the same doses. Patients completed the inflammatory bowel disease questionnaire (IBDQ) and the short-form (SF-36) quality of life surveys and CDAI scores were assessed pretreatment, every 4 weeks on therapy and 4 weeks after completion of the study drug. Drug was administered by mouth each evening for a 12-week period. RESULTS: Seventeen patients with a mean CDAI score of 356+/−27 were enrolled. CDAI scores decreased significantly (P=0.01) with LDN, and remained lower than baseline 4 weeks after completing therapy. Eighty-nine percent of patients exhibited a response to therapy and 67% achieved a remission (P<0.001). Improvement was recorded in both quality of life surveys with LDN compared with baseline.

No laboratory abnormalities were noted.

Forty subjects with active Crohn's disease were enrolled in the study. Randomized patients received daily oral administration of 4.5-mg naltrexone or placebo. Providers and patients were masked to treatment assignment. The primary outcome was the proportion of subjects in each arm with a 70-point decline in Crohn's Disease Activity Index score (CDAI). The secondary outcome included mucosal healing based upon colonoscopy appearance and histology. Eighty-eight percent of those treated with naltrexone had at least a 70-point decline in CDAI scores compared to 40% of placebo-treated patients (p=0.009). After 12 weeks, 78% of subjects treated with naltrexone exhibited an endoscopic response as indicated by a 5-point decline in the Crohn's disease endoscopy index severity score (CDEIS) from baseline compared to 28% response in placebo-treated controls (p=0.008), and 33% achieved remission with a CDEIS score <6, whereas only 8% of those on placebo showed the same change. Fatigue was the only side effect reported that was significantly greater in subjects receiving placebo.

Forty-two IBS patients participated in an open-label study. Participants received 0.5 mg PTI-901/day for 4 weeks and were evaluated during baseline, during treatment, and at 4-week follow-up. Patients recorded degree of abdominal pain, stool urgency, consistency, and frequency. Primary outcomes were number of pain-free days and overall symptom relief, evaluated by a global assessment score. Data were analyzed per protocol. Global assessment improved in 76% of 42 patients. During treatment, the mean weekly number of pain-free days increased from 0.5+/−1 to 1.25+/−2.14 (P=0.011). There were no significant adverse reactions. PTI-901 improves pain and overall feeling, and is well tolerated by IBS patients.

Diabetic Neuropathy 63-year-old male, diagnosed with diabetic neuropathy for the last six years was prescribed one or two tablets every four to six hours as needed for pain. Patient takes between 4 to 8 tablets a day. Started 4.5 mg of IMMEDIATE RELEASE NALTREXONE in March of 2015 and within 3 days was able to cut down the number of pills in half within 8 weeks patient stopped all pain medication, additional benefits included resolutions of RLS.

Fibromyalgia

Thirty-one women with fibromyalgia participated in the randomized, double blind, placebo-controlled, and counter-balanced, crossover study. During the active drug phase, participants received 4.5 mg of oral naltrexone daily. An intensive longitudinal design was used to measure daily levels of pain. When contrasting the condition end points, we observed a significantly greater reduction of baseline pain in those taking low-dose naltrexone than in those taking placebo (28.8% reduction versus 18.0% reduction; P=0.016). Low-dose naltrexone was also associated with improved general satisfaction with life (P=0.045) and with improved mood (P=0.039), but not improved fatigue or sleep. Thirty-two percent of participants met the criteria for response (defined as a significant reduction in pain plus a significant reduction in either fatigue or sleep problems) during low-dose naltrexone therapy, as contrasted with an 11% response rate during placebo therapy (P=0.05). Low-dose naltrexone was rated equally tolerable as placebo, and no serious side effects were reported.

Ten women meeting criteria for fibromyalgia and not taking an opioid medication were dosed with Immediate release Naltrexone, in addition to antagonizing opioid receptors on neurons, also inhibits microglia activity in the central nervous system. At doses (4.5 mg), Immediate release naltrexone may inhibit the activity of microglia and reverse central and peripheral inflammation. The results showed that Immediate release naltrexone at 4.5 mg reduced fibromyalgia symptoms in the entire cohort, with a greater than 30% reduction of symptoms over placebo. In addition, laboratory visits showed that mechanical and heat pain thresholds were improved by the drug. Side effects (including insomnia and vivid dreams) were rare, and described as minor and transient. Baseline erythrocyte sedimentation rate predicted over 80% of the variance in drug response. Individuals with higher sedimentation rates (indicating general inflammatory processes) had the greatest reduction of symptoms in response to Immediate release low-dose naltrexone. Which confirms the ability of Immediate release naltrexone to decree pain and inflammation.

Hashimoto's Thyroiditis

A 45-year-old woman diagnosed with Hashimoto's Mar. 10, 2019 Low energy, nerve pain, development of metabolic syndrome (insulin resistance), folliculitis that had not healed after 4 months, even after 28 days on an oral antibiotic, reduction in T3 hormone levels (which caused me to switch from synthroid to Nature Throid in order to optimize levels of T4 and T3 hormones). Started IMMEDIATE RELEASE NALTREXONE 1.5 mg January of 2015. Prior to starting IMMEDIATE RELEASE NALTREXONE patient was taking Advair, Nasacort, Albuterol, in addition to thyroid hormone, zyrtec, omeprazole, atorvastatin, metformin, and several supplements. After starting IMMEDIATE RELEASE NALTREXONE, patient was able to go off the Advair, Nasacort, and Albuterol. Patients stated sleep quality has improved, energy levels have increased, and allergy symptoms have dramatically decreased, and has not suffered from asthma attacks since starting. No longer has pins-and-needles pain in her feet anymore, and the folliculitis finally healed after taking IMMEDIATE RELEASE NALTREXONE for a few weeks. Latest lab work was normal in all areas.

A 40 year old man was diagnosed October 2011 with Hashimoto Thyroiditis, but believes that his auto-immune disease has progressed and stated over the last 2 years has battled Insomnia, extreme fatigue, bed bound for months at a time, anger, severe depression, brain fog, irritability and neck & back-muscle pain, and no longer responded to synthetic hormone like L-Thyroxin and Euthyrox. Started 1.5 mg of IMMEDIATE RELEASE NALTREXONE for 2 months then 3 mg and continues on 3 mg in morning and 1 mg at night side effect strange dreams. It took weeks to get my energy back and for the depression to go away. Patient was taking L-thyroxine and pain medications and 75 mg Zoloft. Patient is off all medication accept IMMEDIATE RELEASE NALTREXONE and back at work.

A 50 year old woman diagnosed with hyopthyroid since 1992, and diagnosed July 2013 Hashimoto's, MTHFR, adrenal fatigue, estrogen dominance, low B12, low D Patients started at 1.5 mg for 2 weeks then 3 mg for 4 weeks and 4.5 mg and continues on IMMEDIATE RELEASE NALTREXONE today. Patients was taking Synthroid 150 mcg, Compounded T3 25 mcg, Progesterone 150 mg, Plus lots of supplements like Magnesium, D3, Methyl B12, Methyl folate, Selenium, E, Amino Restore, CLA, NAC, DE, Adaptacin. Patients states she has regained energy, stamina, and am gaining my strength back, chronic 13 yr hip pain in very minimal, ear discharge stopped and gums do not bleed, Neck pain is gone, has stopped pain pills, TgAb lowered from 77 to <1, TPO lowered from 229 to 203. Patient continues on 4.5 mg IMMEDIATE RELEASE NALTREXONE has stopped T3, decreased Synthroid from 150 to 50 and B12 went from 300 to 1785 after starting IMMEDIATE RELEASE NALTREXONE and IMMEDIATE RELEASE NALTREXONE helped my absorption issues and conversion of T4 to T3.

A 39-year-old woman diagnosed with Hashimoto's her TPO levels were 350 when initiated T3/T4/19 mcg capsules and Immediate release IMMEDIATE RELEASE NALTREXONE 4.5 mg in August 2011. Patients TPO levels returned to normal and patient reduced T3 to 2.25 mg and continues on 4.5 mg of IMMEDIATE RELEASE NALTREXONE Shingles, or Herpes Zoster A 45-year-old woman diagnosed with Shingles in 2010 over 18 months had 8 major outbreaks, and was treated with acyclovir, and valacyclovir, as the outbreaks continued they prescribed Lidocaine patches and pain medications. In order to help reduce the pain and the duration of shingles, Started 4.5 mg of IMMEDIATE RELEASE NALTREXONE nightly in 2013 and have not had a single outbreak, additional benefit have not even gotten a cold Inflammatory Bowel Disease A 16 year old boy diagnosed with Ulcerative Colitis in 2007 patient when first seen had lost 30 lb. and anemic, and surgery was being recommended, school attendance was sporadic. Patients was prescribed Remicade and GI specialists wanted to increase the dose and frequency of treatments. In May of 2007 patient started a high corroborate diet protocol and 4.5 mg of IMMEDIATE RELEASE NALTREXONE at bedtime over the next five months patient gained 4.5 mg IMMEDIATE RELEASE NALTREXONE, returned to school with attendance 100 percent, first time since in two years he was able to run track and cross-country without missing an event. Patient continues on diet protocol plus 4.5 mg of IMMEDIATE RELEASE NALTREXONE Myasthenia Gravis A 68 year old woman has suffered with myasthenia gravis for over 20 years with effect on her eyesight, chewing, swallowing and. Weakness and numbness of both legs and arms. Patient started IMMEDIATE RELEASE NALTREXONE at 4.5 mg per day at bedtime. Over the next 3 weeks her eyesight began to improve as well as the here other symptoms and her doctors said she was symptom free first time in over 20 years. Patient traveled out of the US and ran out of her IMMEDIATE RELEASE NALTREXONE and her symptoms began to return within 72 hours the worst was the double vision and muscle weakness. When she returned to the United States she immediately resumed her Immediate release naltrexone treatment and has had no attacks since.

Multiple Sclerosis

A Pilot Trial of Low-Dose Naltrexone in Primary Progressive Multiple Sclerosis

A sixth month phase II multicenter-pilot trial with a low dose of the opiate antagonist Naltrexone (LDN) has been carried out in 40 patients with primary progressive multiple sclerosis (PPMS). The primary end points were safety and tolerability. Secondary outcomes were efficacy on spasticity, pain, fatigue, depression, and quality of life. Clinical and biochemical evaluations were serially performed. Protein concentration of beta-endorphins (BE) and mRNA levels and allelic variants of the mu-opioid receptor gene (OPRM1) were analyzed. Results Five dropouts and two major adverse events occurred. The remaining adverse events did not interfere with daily living. Neurological disability progressed in only one patient. A significant reduction of spasticity was measured at the end of the trial. BE concentration increased during the trial, but no association was found between OPRM1 variants and improvement of spasticity. Our data clearly indicate that LDN is safe and well tolerated in patients with PPMS.

Pilot Trial on Low-Dose Naltrexone and Quality of Life in Multiple Scleroses with 80 Patients:

To evaluate the efficacy of 4.5 mg nightly naltrexone on the quality of life of multiple sclerosis (MS) patients. This single-center, double-masked, placebo-controlled, crossover study evaluated the efficacy of 8 weeks of treatment with 4.5 mg nightly naltrexone (low-dose naltrexone, LDN) on self-reported quality of life of MS patients. RESULTS: Eighty subjects with clinically definite MS were enrolled, and 60 subjects completed the trial. Ten withdrew before completing the first trial period: 8 for personal reasons, 1 for a non-MS-related adverse event, and 1 for perceived benefit. Database management errors occurred in 4 other subjects, and quality of life surveys were incomplete in 6 subjects for unknown reasons. The high rate of subject dropout and data management errors substantially reduced the trial's statistical power. LDN was well tolerated, and serious adverse events did not occur. LDN was associated with significant improvement on the following mental health quality of life measures: a 3.3-point improvement on the Mental Component Summary score of the Short Form-36 General Health Survey (p=0.04), a 6-point improvement on the Mental Health Inventory (p<0.01), a 1.6-point improvement on the Pain Effects Scale (p=0.04), and a 2.4-point improvement on the Perceived Deficits Questionnaire (p=0.05). LDN significantly improved mental health quality of life indices. Further studies with LDN in MS are warranted.

Retrospective Chart Review of MS Patients Receiving Low Dose Naltrexone (LDN) to Assess Safety, Tolerability, and Effect on Fatigue.

This study investigated the safety, tolerability, and benefits (fatigue, reduction) of LDN in patients with MS. It reviewed the number of patients who stopped taking LDN and if there were specific reasons for stopping the LDN. The frequency and variety of side effects that were specific to LDN use are reported._A retrospective review was performed on 435 charts of MS patients who were seen in the Penn State Hershey out-patient Multiple Sclerosis Clinic between Jan. 1, 2005 and May 31, 2012. There were 215 MS patients having exposure to LDN during the time of this study._RESULTS: The study confirmed an improvement in quality of life with the use of LDN over a long period of time. In addition to the assessment we review Brain MRIs and Spinal Cord MRIs that were obtained as part of the clinical status of the patient and standard of care.

A 42-year-old woman with M.S. of four years was started on 1.5 mg of Immediate release IMMEDIATE RELEASE NALTREXONE for two weeks then increased to 3 mg for two weeks and has been on IMMEDIATE RELEASE NALTREXONE at 4.5 mg for seven months. Her M.S. is of the fast deteriorating type with increasing weakness, spasticity and incoordination of her arms and legs with some cognitive ability deterioration apparent to her physicians-on each two months follow-up visit. Over a number the last six months since starting the IMMEDIATE RELEASE NALTREXONE, the disease has stabilized and the progressive deterioration has stopped.

A 70-year-old woman one with M.S. of 35 years was started on 3 mg of Immediate release IMMEDIATE RELEASE NALTREXONE for 30 days then increased to 4.5 mg and has taken IMMEDIATE RELEASE NALTREXONE for two years. Her M.S. has been of the slow deteriorating type with increasing weakness, spasticity and incoordination of her arms and legs with deterioration of both eyesight and connectivity ability and deterioration apparent to her physicians on each six-month follow-up visit. Patient was homebound and wheelchair bound at the time she started Immediate release IMMEDIATE RELEASE NALTREXONE at bedtime. Over the next three months she regained her ability to see and walk and her cognitive ability improved as well, the disease has stabilized and the progressive deterioration has stopped.

A 54-year-old man with MS of 8 years was started on 4.5 mg of Immediate release IMMEDIATE RELEASE NALTREXONE. Patients was diagnosed with was relapsing remitting M.S. in 2008 has been of the slow deteriorating type with increasing weakness, spasticity and incoordination of his arms and legs with both deteriorations apparent to his physician on each six month follow up. Patient has been treated with Tysabri and Copaxone and they were getting ready to change his medicine once again as it was no longer effective so patient decided to begin treatment with Immediate release IMMEDIATE RELEASE NALTREXONE. Over the last two and a half years since starting the IMMEDIATE RELEASE NALTREXONE, the disease has stabilized and the progressive deterioration has stopped and his last MRI showed brain lesion healing.

A 49 year old woman diagnosed with Relapsing Remitting MS in June 1999, prescribed a number of medications from January 1999 through September 20012 which included Avonex, Copaxone, Beta-Seron, Prednisone, 11 mg Baclofen twice a day from 1999-2001. In September of 2002 was prescribed Topamax 100 mg after patients suffered from 3 seizures. Patient was prescribed 4.5 Immediate release IMMEDIATE RELEASE NALTREXONE with Topamax and patient continue both Topamax until 2006 at which time patients discontinued the use of Topamax and continues with 4.5 mg of IMMEDIATE RELEASE NALTREXONE taken at bedtime with Vitamin D one a day and Firs oil. When patient started IMMEDIATE RELEASE NALTREXONE in 2002 over the next few months few spams, increasing body strength, less numbness and tingling, fewer headaches. Patient has not had a one relapse since starting IMMEDIATE RELEASE NALTREXONE and MRI over the last 8 years showed no progression of the disease and continues of 4.5 mg Immediate release IMMEDIATE RELEASE NALTREXONE.

A 33 year old woman diagnosed in 2001 Relapsing Remitting MS, and started on Avonex from 2002-mid 2003 with no major relapse. By Mid 2003 relapses were more frequent and started on Reib January of 2004 patients was laid off from her job due to MS symptoms that included poor balance, bladder problems, deteriorating vision and handwriting. Patient became wheelchair bound in March of 2004 due to leg weakness. Patients original doctor refused to prescribe IMMEDIATE RELEASE NALTREXONE. Patient in July 2004 was prescribed IMMEDIATE RELEASE NALTREXONE 3 mg nightly within 3 days spams subsided and bladder urgency was reduced but all of my other MS related symptoms were improving. Patient was walking again with a cane for assistance within 10 days of starting IMMEDIATE RELEASE NALTREXONE. In August of 2004 IMMEDIATE RELEASE NALTREXONE was increased to 4.5 mg nightly with minimal side effects some insomnia the 30 days but then subsided. Patient last update was 2010 and was still driving, living alone and have some balance issues no relapses continue to take 4.5 mg nightly.

A 55-year-old male was diagnosed with Relapsing Remitting MS in 1998, and Secondary Progressive in 2002. Patient's chief symptoms extreme mixed sleep apnea, chronic obstructive pulmonary diseases (COPD) inability to walk, total deafness in left ear and inability to concentrate for any period of time. Patient prior to starting IMMEDIATE RELEASE NALTREXONE was from February 1998-August 2001 Avonex, 1999 to 2000 Copaxone and Avonex together; March 2002-June of 2005 Rebit and September 2001 to 2002 Cytoxan (chemotherapy) August 2001 plasma exchange for eleven days. From 2001-2005 multiple infusion of Solmefrol IV steroids (minimum of 4 times a year) Gabapentin 3 times a day, Clonazpam 1 time nightly, Effexor XR 2 times a day 37 mg, Acicept 1 time a day 11 mg, Flomax 1 time a day 11 mg Baclofen 3 times a day 10 MEQ CAP, and Furosemide 1 time a day 40 mg. As of June of 2005 was on oxygen 24/7, wheelchair bound, MS flairs one a month. Patient in July of 2005 was prescribed 1.5 mg of IMMEDIATE RELEASE NALTREXONE one time a day at bedtime increasing to 3 mg of IMMEDIATE RELEASE NALTREXONE within 7 days stopped taking Rebit, no real improvement in the first three months accept no flair of MS. Patient improved slowly over the next 3 months, was able to take time off oxygen to extended periods of time, strength returned in in legs and arms and was able to take short walks with walker, then longer walks then upgraded from wheelchair to cane. Sleep began to improve. At six month all my tests results improved. Patients continues to do well is driving and only taking 4.5 mg IMMEDIATE RELEASE NALTREXONE and Vitamin D Supplements September 2012.

A 46 year old female, was diagnosed with relapsing remitting MS in 2002 and managed the symptoms on a combination of MS drugs until 2010 when she was forced to go part time due difficulty with brain fog, severe insomnia, severe fatigue and debilitating frequent exacerbations. Also poor sleep quality. Treatment Plan: January 2005 IMMEDIATE RELEASE NALTREXONE 1.5 mg increasing to 4.5 mg nightly at bedtime. In addition to IMMEDIATE RELEASE NALTREXONE patient was prescribed bio-identical progesterone and estriol 8 mg, Cortef for adrenal support MS, response, Patient began sleeping better within 2 week, Energy levels improved and brain fog, started to clear within a month, Exacerbations became less frequent and have stopped, patient returned to work within 12 months of starting the protocol patient has been back at work for 5 years without an exacerbation A 54-year-old male diagnosed with secondary-progressive multiple sclerosis (SPMS) in 2006 current treatment included Tysabri infusions difficulty walking, severe heat sensitivity unable to work. In July of 2009 patient started Immediate release IMMEDIATE RELEASE NALTREXONE at 1.5 mg for one week to 3 mg in week two patient saw immediate improvement increased stamina, was able to return to work, in January of 2011 MRI showed reduced plaque and lesion size This study investigated the safety, tolerability, and benefits (fatigue, reduction) of IMMEDIATE RELEASE NALTREXONE (LDN) in patients with MS. It reviewed the number of patients who stopped taking IMMEDIATE RELEASE NALTREXONE (LDN) and if there were specific reasons for stopping the IMMEDIATE RELEASE NALTREXONE (LDN). The frequency and variety of side effects that were specific to IMMEDIATE RELEASE NALTREXONE (LDN) use are reported. A retrospective review was performed on 435 charts of MS patients who were seen in the Penn State Hershey out-patient Multiple Sclerosis Clinic between Jan. 1, 2005 and May 31, 2012. There were 215 MS patients having exposure to IMMEDIATE RELEASE NALTREXONE (LDN) during the time of this study. RESULTS: The study confirmed an improvement in quality of life with the use of IMMEDIATE RELEASE NALTREXONE (LDN) over a long period of time. In addition to the assessment we review Brain MRIs and Spinal Cord MRIs that were obtained as part of the clinical status of the patient and standard of care. There were essentially no MRIs obtained immediately before IMMEDIATE RELEASE NALTREXONE (LDN) was started as would have been ideal in a prospective study.

The average number of days of the Brain MRI before treatment with IMMEDIATE RELEASE NALTREXONE (LDN) was started was 444 days with a maximum of 4751 days. The average number of days to the latest Brain MRI after IMMEDIATE RELEASE NALTREXONE (LDN) was started was 708 with a maximum of 1772 days of 215 patients on IMMEDIATE RELEASE NALTREXONE (LDN) 113 MRI scans showed stable, 14 showed improvement, 28 slightly worse. The Slightly Worse MRI series indicated that new but inactive lesion(s) were identified when compared to the pretreatment study MRI. On the quality of life surveys showed 83 patients said they had improved, 92 patients said they were stable and 9 worse. The remainder of the patients did not continue on IMMEDIATE RELEASE NALTREXONE (LDN).

Psoriatic Arthritis

A 55 Year old man with psoriatic arthritis for 8 years and was being treated with Humira and was concerned about the side effects of the drug as he had been hospitalized four times over a 18 month period for Pneumonia and kidney infections and decided to begin treatment with IMMEDIATE RELEASE NALTREXONE. He started on 4.5 mg of Immediate release IMMEDIATE RELEASE NALTREXONE fat bedtime. Within 10 days of starting IMMEDIATE RELEASE NALTREXONE he was able to discontinue all paid medications as well as the Humira and over the last six months since starting the IMMEDIATE RELEASE NALTREXONE, the disease has stabilized and the progressive deterioration has stopped.

Rheumatoid Arthritis (RA)

A 40 year old woman diagnosed with Rheumatoid Arthritis in 2006 and was being treated with methotrexate and plaquenil but patients continued with pain and fatigue. In April of 2009 patients started treated with 1.5 mg of Immediate release IMMEDIATE RELEASE NALTREXONE and titrated up to 4.5 mg over two months. Tried stopping methotrexate in July 2009 starting have bad flares and again started methotrexate Successfully discontinued methotrexate March of 2010 and then discontinued plaquenil in October of 2010 patient continues on 4.5 mg of Immediate release IMMEDIATE RELEASE NALTREXONE.

Systemic Sclerosis (Scleroderma)

A 44 year old male diagnosed with Systemic Lupus by Rheumatologist in in 2005 patient suffered from malar rash, Reynaud's Disease & Arthritic Pain, difficulty with mobility multiple hospital admission since 2005 fluid on the lungs and skin blister: began treatment of 3 mg of IMMEDIATE RELEASE NALTREXONE March 2013 increasing to 4.5 mg in May of 2013. Patient within three weeks after beginning treatment with IMMEDIATE RELEASE NALTREXONE had improved mobility, within 4 months joints improved walking daily, skin cleared almost 100% blood results improving. Patient before starting IMMEDIATE RELEASE NALTREXONE was on Imuran 75 mg, treated with high dose steroids, and ace inhibitor, ramipril. Patients continues on take 4.5 mg of IMMEDIATE RELEASE NALTREXONE and has had no hospital stays since March of 2013.

A 32 year old female diagnosed with systemic lupus with psoriasis, IBS and chronic fatigue develops joint pain, increasing abdominal pain and malar rash Patient refused immunosuppressing drugs and tried supplements and healthy diet • Patient contracted MRSA in 2010 in hospital • MRSA treated with oral drugs twice, then with IV drugs patient developed sepsis. Infection kept recurring boils. • Antibiotics work, but patient continued to get sicker and sicker with worsening symptoms and rising ANA although no organ damage.

Unable to take immunomodulating drugs due to MRSA recurrence and intolerant to others standard treatments for lupus, her doctors informed here that they could offer no help and she needed to put her affairs in order as it was only a matter or time. In 2012 office, she receives: HBO, acupuncture, supplement tailoring, treatment for mercury toxicity, food elimination diet then rotation, treatment for yeast overgrowth; • She is started on IMMEDIATE RELEASE NALTREXONE 1.5 mg, but is unable to take it due to insomnia and pruritis. • IMMEDIATE RELEASE NALTREXONE changed to liquid form and started at 0.5 mg, IMMEDIATE RELEASE NALTREXONE decreased to 0.1 mg and increased by 0.1 mg once a week until she reached 1.5 mg, which is where she stays. Lupus, in remission currently still on IMMEDIATE RELEASE NALTREXONE, supplements, healthy diet and lifestyle No recurrence of MRSA in 8 years No signs or symptoms of lupus and normal ANA for 7 years Intestinal symptoms resolved for 2 years with some issues when patient does not stay on a healthy diet. Psoriasis mostly resolved.

Fibromyalgia

Twenty-five patients diagnosed with fibromyalgia treatment with (Immediate release naltrexone) LDN open label study carried out at a single center Of the 22 patients completing the study, using 4.5 mg Immediate release naltrexone 7 (32%) remained on naltrexone monotherapy throughout the study. At Month 3, a 19.5% overall improvement in FIQR was "The patients reported decreases in anxiety, pain, and sleeping habits from baseline reported. Eleven patients (50%) had an average of a 41% improvement in FIQR.

Double Blind Crossover to determine whether low dosages (4.5 mg/day) of Immediate release naltrexone reduce fibromyalgia severity as compared with the nonspecific effects of placebo. When contrasting the condition end points, we observed a significantly greater reduction of baseline pain in those taking low-dose naltrexone than in those taking placebo (28.8% reduction versus 18.0% reduction; P=0.016). Low-dose naltrexone was also associated with improved general satisfaction with life (P=0.045) and with improved mood (P=0.039), but not improved fatigue or sleep. Thirty-two percent of participants met the criteria for response (defined as a significant reduction in pain plus a significant reduction in either fatigue or sleep problems) during low-dose naltrexone therapy, as contrasted with an 11% response rate during placebo therapy (P=0.05). Low-dose naltrexone was rated equally tolerable as placebo, and no serious side effects were reported.

A Woman aged 53 was diagnosed in 1998 Fibromyalgia and Epstein Barr, had to quit work, in pain and very depressed. Various treatments over the years for pain prescribed and other problems with the disease. Was prescribed IMMEDIATE RELEASE NALTREXONE 0.5 mg in 2004 and saw improvement by the following day slight, continued to see improvement and increased to 3 mg of the next 60 days, has more energy and the pain level has decreased by 90% and cognitive ability and mood is better and no longer need to take anti-depressants.

Rheumatoid Arthritis

A 59 year old male diagnosed 5 years ago with RA was treated with Methotrexate 25 mg per week and Remicade 300 U every 6 weeks, the fatigue and pain continued, along with the inflammation and general weakness. Sleep disturbed nightly due to pain in my shoulders and hips. Patient felt her life was not acceptable and none of the immunosuppression drugs were helping. In 2007 patient started 4.5 mg of Immediate release naltrexone at bedtime and within 7 days patient stooped all traditional RA medications. Within two weeks patient stopped even ibuprophen. Rheumatoid factor has gone from 127 to 66 in 4 months and has stayed stable. Fatigue is gone. Occasionally patient has pain but it is easily controlled with a normal dosage of ibuprophen.

A 63-year-old female, diagnosed with RA in 1999 stayed very active until 2005 on a combination of Methotrexate and Prednisone but was have difficulty maintaining her business due to fatigue and severe joint pain with deformity of her hands and elbows. Patient was told to increase her does and start a second immunomodulating drug. Patient no longer wanted to continue with immunosuppression drug or steroids due to the side effects. In 2008 patient started a new protocol which included dietary changes, supplements, acupuncture, microcurrent therapy, toxicity testing and treatment, Bio-identical hormones, adrenal support and thyroid started, Immediate release naltrexone started at 4.5 mg RA, discontinued the use of all other RA medication over a three week period. 7 years later, still not on any other drugs, RA has not advanced; she has no pain that can't be handled with aspirin.

The following references are herein incorporated by reference in their entirety.
1. Pellett P E, Ablashi D V, Ambros P F, Agut H, Caserta M T, et al. Chromosomally integrated human herpesvirus 6: questions and answers. Rev Med Virol. 2012 May. 22(3): 144-55.
2. Agut H. Deciphering the clinical impact of acute human herpesvirus 6 (HHV-6) infections. J Clin Virol. 2011 November. 52(3):164-71.
3. Strong M J, O'Grady T, Lin Z, Xu G, Baddoo M, Parsons C, et al. Epstein-Barr Virus and Human Herpesvirus 6 Detection in a non-Hodgkin's Diffuse Large B-Cell Lymphoma Cohort using RNA-Seq. J Virol. 2013 Sep. 18.
4. Merk J, Schmid F X, Fleck M, Schwarz S, Lehane C, Boehm S, et al. Fatal pulmonary failure attributable to viral pneumonia with human herpes virus 6 (HHV6) in a young immunocompetent woman. J Intensive Care Med. 2005 September-October. 20(5):302-6.
5. Harris R C. Long-term effects of human herpesvirus 6 infection. Pediatrics. 2008 September. 122(3):679.
6. Broccolo F, Drago F, Cassina G, Fava A, Fusetti L, Matteoli B, et al. Selective reactivation of human herpesvirus 6 in patients with autoimmune connective tissue diseases. J Med Virol. 2013 November. 85(11):1925-34.
7. Singh N. Infections with Human Herpesvirus 6, 7, and 8 after hematopoietic stem cell or solid organ transplantation. In: Bowden R, Ljungman P, Paya C. Transplant Infections. 2nd. Philadelphia: Lippincott Williams & Wilkins; 2004:365-374.
8. Betts B C, Young J A, Ustun C, Cao Q, Weisdorf D J. Human herpesvirus 6 infection after hematopoietic cell transplantation: is routine surveillance necessary?. Biol Blood Marrow Transplant. 2011 October. 17(10):1562-8.
9. Buyse S, Roque-Afonso A M, Vaghefi P, Gigou M, Dussaix E, Duclos-Vallée J C, et al. Acute hepatitis with periportal confluent necrosis associated with human herpesvirus 6 infection in liver transplant patients. Am J Clin Pathol. 2013 September. 140(3):403-9.
10. Kunisaki Y, Goto H, Kitagawa K, Nagano M. Salazosulfapyridine induced hypersensitivity syndrome associated with reactivation of humanherpes virus 6. Intern Med. 2003 February. 42(2):203-7.
11. Murakami Y, Tanimoto K, Fujiwara H, An J, Suemori K, Ochi T, et al. Human herpesvirus 6 infection impairs Toll-like receptor signaling. Virol J. 2010 May 10. 7:91.
12. De Bolle L, Naesens L, De Clercq E. Update on human herpesvirus 6 biology, clinical features, and therapy. Clin Microbiol Rev. 2005 January. 18(1):217-45.
13. Ward K N, Leong H N, Nacheva E P, Howard J, Atkinson C E, Davies N W, et al. Human herpesvirus 6 chromosomal integration in immunocompetent patients results in high levels of viral DNA in blood, sera, and hair follicles. J Clin Microbiol. 2006 April. 44(4):1571-4.
14. Hasegawa A, Yasukawa M, Sakai I, Fujita S. Transcriptional down-regulation of CXC chemokine receptor 4 induced by impaired association of transcription regulator YY1 with c-Myc in human herpesvirus 6-infected cells. J. Immunol. 2001 Jan. 15. 166(2):1125-31.
15. Kumagai T, Yoshikawa T, Yoshida M, Okui T, Ihira M, Nagata N, et al. Time course characteristics of human herpesvirus 6 specific cellular immune response and natural killer cell activity in patients with exanthema subitum. J Med Virol. 2006 June. 78(6):792-9.

16. Agward, Y. and A. Lucille, 2005. Low dose naltrexone therapy in multiple sclerosis, Medical Hypotesis, 64 (4): 721-724.
17. Honar, H., K. Riazi, H. Homayon and H. Sadeghipour, 2004. Ultra low dose naltrexone potentiates the anti convulsant effect of low dose morphine on clonic seizures, Neuroscience, 3 (129): 733-742.
18. Revital, K., E. Timny and R. Grenshpon, 2003. Low dose naltrexone for the treatment of irritable bowel syndrome. The Am. J. Gastroenterol., 98 (9): s268.
19. Makman, M., 1994. Morphine receptors in immunocytes and neurons, Adv. Neuroimmunol., 4: 69-82.
20. Roys, Loh H., 1996. Effects of opioids on the immune system. Neurochem Res., 21: 1375-1386.
21. Manual, P., L. Marion and L. Jean-Marie, 1995. Low dose naltrexone effects on plasma chemisteies and clinical symptoms in autism: A double blind, placebo-controlled study, psychiatry Res., 58 (3):191-201
22. Sabine, A. J., A. Arnold, 1996. Anxiety and pain: Attentional and endorphinergic influences, Pain, 66 (2-3): 145-150.
23. Paolo, M., G. Edward and F. James, 2004. chronic very low dose naltrexone administration attenuates opioid withdrawal expression, Biological Psychiatry, 56 (4): 261-268.
24. Ian, S. Z., J. Patricia and Maclaughlin, 1987. Endogenous opioid systems regulate cell proliferation in the developing rat brain. Brain Res., 412 (1): 68-72.
25. Arntz, A., M. Harald and P. Dejong, 1993. Opioid antagonist affects behavioral effects of exposure in vivo. J. Consul. Clin. Psychol., 61 (5): 865-870.
26. Roys, Loh H., 1996. Effects of opioids on the immune system. Neurochem Res., 21:1375-1386.
27. Vanderah, T. and L. Burns, 2004. Ultra low dose naltrexone plus morphine blocks thermal hyperalgesia and attenuates mechanical hypersensitivity in a neuropathic pain model, Pain, 5 (3): s59.
28. Rockville, Shekelle P., 2003. Best case series for the use of immune-augmentation therapy and naltrexone for the treatment of cancer, Summary Evidence Report, Evidence Report/Technology Assessment: AHRQ Publication. NO3-EO29 April
29. Cantilena, Jr., C. Wright and C. Miller, 2004. Effects of low dose naltrexone on analgesia produced by hydrocodone. Clinical Pharmacol. Therapeutics, 75 (2): 71
30. Hunt P W, Martin J N, Sinclair E, Bredt B, Hagos E, Lampiris H, Deeks S G. T Cell Activation Is Associated with Lower CD4+ T Cell Gains in Human Immunodeficiency Virus-Infected Patients with Sustained Viral Suppression during Antiretroviral Therapy. J Infect Dis. 2003; 187:1534-43.
31. Neuhaus J, Jacobs D R, Jr, Baker J V, Calmy A, Duprez D, La Rosa A, Kuller L H, Pett S L, Ristola M, Ross M J, Shlipak M G, Tracy R, Neaton J D. Markers of inflammation, coagulation, and renal function are elevated in adults with HIV infection. J Infect Dis. 2010; 201:1788-95.
32. Kuller L H, Tracy R, Belloso W, De Wit S, Drummond F, Lane H C, Ledergerber B, Lundgren J, Neuhaus J, Nixon D, Paton N I, Neaton J D. Inflammatory and coagulation biomarkers and mortality in patients with HIV infection. PLoS Med. 2008; 5:e203.
33. Favre D, Mold J, Hunt P W, Kanwar B, Loke P, Seu L, Barbour J D, Lowe M M, Jayawardene A, Aweeka F, Huang Y, Douek D C, Brenchley J M, Martin J N, Hecht F M, Deeks S G, McCune J M. Tryptophan catabolism by indoleamine 2,3-dioxygenase 1 alters the balance of TH17 to regulatory T cells in HIV disease. Sci Transl Med. 2010; 2:32ra6.
34. Doitsh G, Cavrois M, Lassen K G, Zepeda O, Yang Z, Santiago M L, Hebbeler A M, Greene W C. Abortive HIV infection mediates CD4 T cell depletion and inflammation in human lymphoid tissue. Cell. 2010; 143:789-801.
35. Hunt P W, Brenchley J, Sinclair E, McCune J M, Roland M, Page-Shafer K, Hsue P, Emu B, Krone M, Lampiris H, Douek D, Martin J N, Deeks S G. Relationship between T Cell Activation and CD4(+) T Cell Count in HIV-Seropositive Individuals with Undetectable Plasma HIV RNA Levels in the Absence of Therapy. J Infect Dis. 2008; 197:126-33.
36. Hatano H, Jain V, Hunt P W, Lee T H, Sinclair E, Do T D, Hoh R, Martin J N, McCune J M, Hecht F, Busch M P, Deeks S G. Cell-Based Measures of Viral Persistence Are Associated With Immune Activation and Programmed Cell Death Protein 1 (PD-1)-Expressing CD4+ T cells. The Journal of infectious diseases 2012
37. Srinivasula S, Lempicki R A, Adelsberger J W, Huang C Y, Roark J, Lee P I, Rupert A, Stevens R, Sereti I, Lane H C, Di Mascio M, Kovacs J A. Differential effects of HIV viral load and CD4 count on proliferation of naive and memory CD4 and CD8 T lymphocytes. Blood. 2011; 118:262-70.
38. Hunt P W, Cao H L, Muzoora C, Ssewanyana I, Bennett J, Emenyonu N, Kembabazi A, Neilands T B, Bangsberg D R, Deeks S G, Martin J N. Impact of CD8+ T-cell activation on CD4+ T-cell recovery and mortality in HIV-infected Ugandans initiating antiretroviral therapy. AIDS. 2011; 25:2123-31.

What is claimed is:

1. A method for treating or preventing an autoimmune and inflammatory diseases chosen from the group consisting of chronic rheumatoid arthritis inflammatory bowel disease multiple sclerosis, Crohn's disease, ulcerative colitis, Hashimoto's thyroiditis, systemic sclerosis, myasthenia gravis, chronic obstructive pulmonary disorder (COPD) and diabetic nephropathy comprising administering to a mammal in need thereof an Immediate release pharmaceutical composition comprising between about 0.01 mg and about 10.0 mg of naltrexone or a pharmaceutically acceptable salt thereof.

2. The method of claim 1, wherein the amount of naltrexone is between about 1.0 mg and about 8.0 mg.

3. The method of claim 1, wherein the amount of naltrexone is between about 0.05 mg and about 6.0 mg.

4. The method of claim 1, wherein the amount of naltrexone is between about 0.05 mg and about 4.5 mg.

5. The method of claim 1, wherein the autoimmune and inflammatory disease is Crohn's disease.

6. The method of claim 1, wherein said administration is once in a 24 hour period.

7. The method of claim 1, wherein said mammal is a human.

8. The method of claim 1, wherein said pharmaceutically acceptable salt is the hydrochloride salt.

9. The method of claim 1, wherein said Immediate release composition releases the pharmaceutically acceptable salt of naltrexone completely within about 60 minutes.

10. The method of claim 1, wherein said administration is chosen from the group consisting of oral, sublingual, subcutaneous, intramuscular, intravenous, topical, local, intratracheal, intranasal, transdermal and rectal administration.

11. The method of claim 1, wherein said Immediate release composition is in the form of a capsules or tablet.

12. The method of claim 1, wherein said Immediate release composition is in the form of a rapidly dissolving film.

* * * * *